(12) United States Patent
Gelfand et al.

(10) Patent No.: US 7,582,300 B2
(45) Date of Patent: *Sep. 1, 2009

(54) MODULATION OF GAMMA DELTA T CELLS TO REGULATE AIRWAY HYPERRESPONSIVENESS

(75) Inventors: Erwin Gelfand, Englewood, CO (US); Willi K. Born, Denver, CO (US); Michael F. Lahn, Denver, CO (US); Arihiko Kanehiro, Okayama (JP)

(73) Assignee: National Jewish Health, Denver, CO (US)

( * ) Notice: Subject to any disclaimer, the term of this patent is extended or adjusted under 35 U.S.C. 154(b) by 457 days.

This patent is subject to a terminal disclaimer.

(21) Appl. No.: 10/808,846

(22) Filed: Mar. 24, 2004

(65) Prior Publication Data
US 2005/0008627 A1    Jan. 13, 2005

Related U.S. Application Data

(63) Continuation of application No. 09/672,865, filed on Sep. 28, 2000, now Pat. No. 6,737,398.

(60) Provisional application No. 60/157,231, filed on Sep. 30, 1999.

(51) Int. Cl.
| | |
|---|---|
| A01N 61/00 | (2006.01) |
| A61K 31/00 | (2006.01) |
| A61K 39/38 | (2006.01) |
| A61K 39/02 | (2006.01) |
| A61K 39/04 | (2006.01) |

(52) U.S. Cl. .............. 424/184.1; 424/234.1; 424/248.1; 424/282.1; 514/1

(58) Field of Classification Search ........................ None
See application file for complete search history.

(56) References Cited

U.S. PATENT DOCUMENTS

| | | | |
|---|---|---|---|
| 5,185,250 A | 2/1993 | Brenner et al. | ............. 435/69.3 |
| 5,340,921 A | 8/1994 | Brenner et al. | ............. 530/350 |
| 5,601,822 A | 2/1997 | Brenner et al. | ........... 424/144.1 |
| 5,639,653 A | 6/1997 | Bloom et al. | ................ 514/102 |
| 6,086,898 A | 7/2000 | DeKruyff et al. | ........ 424/275.1 |
| 6,429,199 B1 | 8/2002 | Krieg et al. | .................... 514/44 |

FOREIGN PATENT DOCUMENTS

WO    WO 99/37319    7/1999

OTHER PUBLICATIONS

Cendron et al. Eur. J.. Immunol. 37:549-565, 2007.*
Sicard et al. J. Immunol. 175:5471-5480, 2005.*
Burks et al. 'Human V gamma 9-V delta 2 cells are stimulated in a cross-reactive fashion by a variety of phosphorylated metabolites.' Eur. J. Immunol. 25(7):2052-2058, 1995.*
Zhang et al. 'Structural Stuidies of Vgamma2vdelta2 T cell Phosphoantigens.' Chem. & Biol. 13:985-992, 2006.*
Bertotto et al., Acta Paediatr. 86:114-5 (1997).
Blond-Elguindl et al., Cell, 75:717-726 (1993).
Bolsmenu et al., Science, 266:1253-1255 (1994).
Born et al., Science, 249:67-69 (1990).
Cady et al., J. Immunol., 165:1-9 (2000).
Chen et al., Clin. Exp. Allergy, 26:295-302 (1996).
Fajac et al., Eur. Respir J., 10:633-638 (1997).
Fu et al., Proc. Natl. Acad. Sci. USA, 90:322-326 (1993).
Fu et al., J. Immunol., 152:1578-1588 (1994).
Fu et al., J. Immunol., 153:3101-3115 (1994).
Fujihashi et al., J. Exp. Med., 175:695-707 (1992).
Hiromatsu et al., J. Exp. Med., 175:49-56 (1992).
Jaffar et al., J. Immunol., 163:6283-6291 (1999).
Jones et al., Prog. Growth Factor Rees, 1:107-22 (1989).
Krejsek et al., Allergy, 53:73-77 (1998).
Lahn et al., J. Immunol., 160:5221-5230 (1998).
Martin et al., Am. J. Physiol. Lung Cell Mol. Physiol., 280:L595-601 (2001).
McMenamin et al., Science, 265:1869-1871 (1994).
Molfino et al., Clin. Exp. Immunol., 104:144-153 (1996).
Munk et al., Int'l Immunol., 9(5):713-720 (1997).
Nebert et al., Biochemical Pharmacol., 53:249-54 (1997).
O'Brien et al., Proc. Natl. Acad. Sci. USA, 89:4348-4352 (1992).
Pawankar et al., J. Allergy Clin. Immunol., 98:S248-62 (1996).
Schauer et al., Clin. Exp. Immunol., 86:440-443 (1991).
Schramm et al., International Conference of the American Thoracic Society; 159:A255 (American Journal of Respiratory and Critical Care Medicine, San Diego, California).
Schramm et al., Am. J. Respir. Cell Mol. Biol., 22:218-225 (2000).
Spinozzi et al., Mol. Med., 1(7):821-826 (1995).
Spinozzi et al., Ann. Intern. Med., 124:223-227 (1996).
Wagner, Am. J. Physiol Heart Circ Physiol., 279:H946-51 (2000).
Wheeler et al., J. Appl. Physiol., 68:2542-9 (1990).
Yanagihara, Allergol Intl., 48:111-9 (1999).
Zuany-Amorim et al., Science, 280:1265-1267 (1998).
Ismaili et al., Human gamma delta T Cells Induce Dendritic Cell Maturation, Clinical Immunology, Jun. 2002, 296-302, vol. 103.
Wang et al., Human V gamma 2 V delta 2 T Cells Produce IFN-gamma and TNF-alpha with an OnOffOn Cycling Pattern in Response to Live Bacterial Products, The Journal of Immunology, 2001, 6195-6201, vol. 167.
Epinosa et al., Y2K+1 state-of-the-art on non-peptide phosphoantigens, a novel category of immunostimulatory molecules, Microbes and Infection, Mar. 2001, 645-654, vol. 3.
Belmant et al., A chemical basis for selective recognition of nonpeptide antigens by human delta T cells, The FASEB Journal, Sep. 2000, 1669-1670, vol. 14.
Lang et al., Early Activation of Human V gamma 9 V delta 2 T Cell Broad Cytotoxicity and TNF Production by Nonpeptidic Mycobacterial Ligands, The Journal of Immunology, 1995, 5986-5994, vol. 154.

* cited by examiner

Primary Examiner—Maher M Haddad
Assistant Examiner—Nora M Rooney
(74) Attorney, Agent, or Firm—Sheridan Ross P.C.

(57) ABSTRACT

Disclosed is a method for regulation of airway hyperresponsiveness by modulating the action of γδ T cells in a patient. Also disclosed are methods for identifying compounds that regulate airway hyperresponsiveness by modulating γδ T cell action.

19 Claims, 10 Drawing Sheets

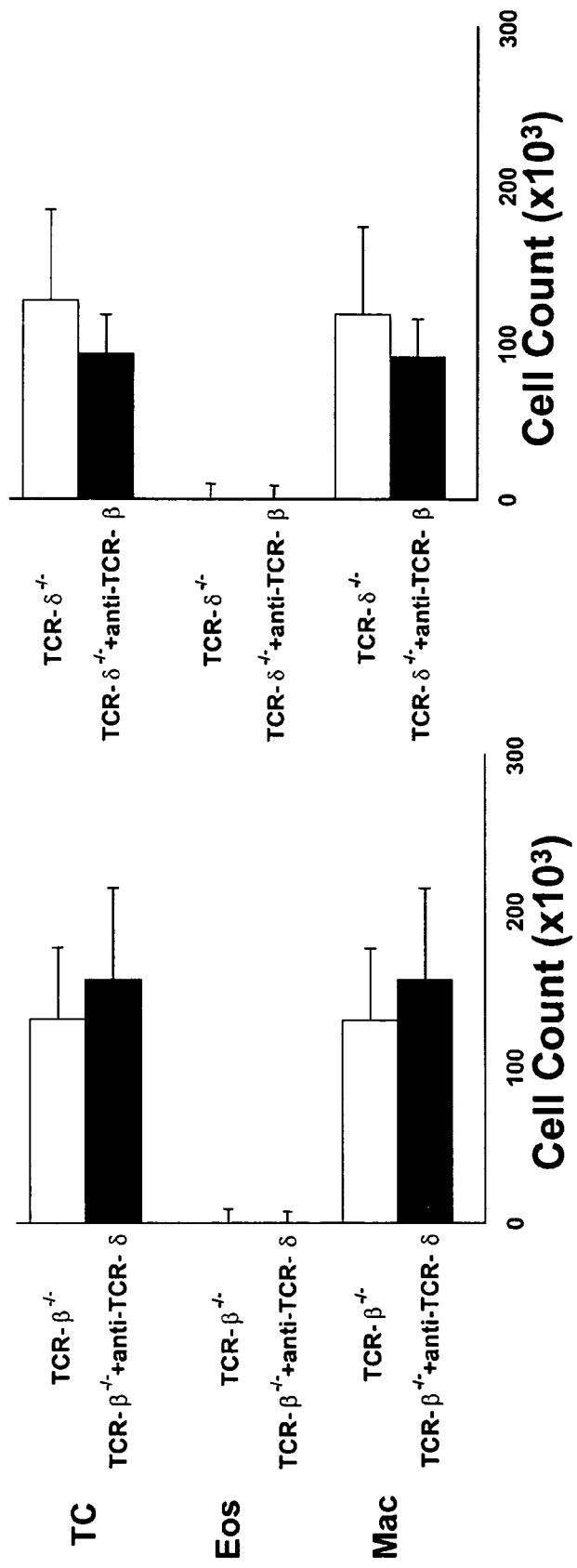

MODULATION OF GAMMA DELTA T CELLS TO REGULATE AIRWAY HYPERRESPONSIVENESS

CROSS-REFERENCE TO RELATED APPLICATIONS

This application is a continuation of U.S. patent application Ser. No. 09/672,865, filed Sep. 28, 2000 now U.S. Pat. No. 6,737,398, which application claims priority under 35 U.S.C. § 119(e) from U.S. Provisional Application Ser. No. 60/157,231, filed Sep. 30, 1999, and entitled "Regulation of Airway Hyperresponsiveness by Modulation of γδ T Cells." The entire disclosure of U.S. patent application Ser. No. 09/672,865 and U.S. Provisional Application Ser. No. 60/157,231 is incorporated herein by reference.

GOVERNMENT RIGHTS

This invention was made in part with government support under NIH Grant HL-36577, NIH Grant AI-40611 and NIH Grant AI-01291, all awarded by the National Institutes of Health. The government has certain rights to this invention.

FIELD OF THE INVENTION

The present invention generally relates to a method to regulate airway hyperresponsiveness by modulating the action of γδ T cells in a patient. The present invention further relates to methods for identifying compounds that regulate airway hyperresponsiveness by modulating γδ T cell action.

BACKGROUND OF THE INVENTION

Diseases involving inflammation are characterized by the influx of certain cell types and mediators, the presence of which can lead to tissue damage and sometimes death. Diseases involving inflammation are particularly harmful when they afflict the respiratory system, resulting in obstructed breathing, hypoxemia, hyperapnia and lung tissue damage. Obstructive diseases of the airways are characterized by airflow limitation (i.e., airflow obstruction or narrowing) due to constriction of airway smooth muscle, edema and hypersecretion of mucus leading to increased work in breathing, dyspnea, hypoxemia and hypercapnia.

A variety of inflammatory agents can provoke airflow limitation including allergens, cold air, exercise, infections and air pollution. In particular, allergens and other agents in allergic or sensitized mammals (i.e., antigens and haptens) cause the release of inflammatory mediators that recruit cells involved in inflammation. Such cells include lymphocytes, eosinophils, mast cells, basophils, neutrophils, macrophages, monocytes, fibroblasts and platelets. Inflammation results in airway hyperresponsiveness (AHR). A variety of studies have linked the degree, severity and timing of the inflammatory process with the degree of airway hyperresponsiveness. Thus, a common consequence of inflammation is airway hyperresponsiveness.

Currently, therapy for treatment of inflammatory diseases involving AHR, such as moderate to severe asthma and chronic obstructive pulmonary disease, predominantly involves the use of glucocorticosteroids and other anti-inflammatory agents. These agents, however, have the potential of serious side effect, including, but not limited to, increased susceptibility to infection, liver toxicity, drug-induced lung disease, and bone marrow suppression. Thus, such drugs are limited in their clinical use for the treatment of lung diseases associated with airway hyperresponsiveness. The use of anti-inflammatory and symptomatic relief reagents is a serious problem because of their side effects or their failure to attack the underlying cause of an inflammatory response. There is a continuing requirement for less harmful and more effective reagents for treating inflammation. Thus, there remains a need for processes using reagents with lower side effect profiles, less toxicity and more specificity for the underlying cause of AHR.

Airway hyperresponsiveness (AHR) is the result of complex pathophysiological changes in the airway. A variety of studies have linked the degree, severity and timing of the inflammatory process with the degree of airway hyperresponsiveness. However, the mechanisms leading to AHR are still poorly understood and can be attributed to both immune-dependent and immune-independent mechanisms. Essentially all of the T cell-mediated effects described so far are in the former category. However, T cells from hyperresponsive mice can increase baseline airway tone in hyporesponsive mice after cell transfer. Because of their constitutive presence in the normal lung, γδ T cells have been investigated with regard to their potential role in airway responses.

γδ T cells have been observed to proliferate and produce cytokines in many diseases. In addition, studies in animal models have provided evidence that these cells contribute to host resistance against infections (Hiromatsu et al., 1992, *J. Exp. Med.* 175:49), and that they can influence inflammation (Fu et al., 1994, *J. Immunol.* 153:3101), epithelial regeneration (Boismenu et al., 1994, *Science* 266:1253), and mucosal tolerance to antigens (Fujihashi et al., 1992, *J. Exp. Med.* 175:695; McMenamin et al., 1994, supra). Investigators are still determining what stimuli trigger γδ T cell reactivity, and to what extent γδ T cell activating stimuli differ from those of αβ T cells and B lymphocytes. It is known that γδ T cells respond during bacterial and viral infections, although they have not been readily linked to antigen-specific adaptive immunity.

A number of studies have investigated the presence and role of γδ T cells in diseases of the airways. Pawankar et al. noted the mucosal changes at the site of allergic inflammation in patients with perennial allergic rhinitis and chronic infective rhinitis includes an oligoclonal expansion and activation of Vγ1/Vδ$^+$ T cells (Pawankar and Ra, 1996, *J. Allergy Clin. Immunol.* 98:S248-62). Molfino et al. showed that much of the γδ T cell population found in broncho alveolar lavage (BAL) fluid in humans derives from clonally expanded T cells (Molfino et al., 1996, *Clin. Exp. Iminunol.* 104:144-153). Spinozzi et al., measuring γδ T cells in the BAL fluid from patients with asthma, concluded that allergen-specific, steroid-sensitive γδ T cells may be one of the cellular components involved in the airway inflammation that characterizes allergic bronchial asthma (Spinozzi et al., 1996, *Ann. Intern. Med.* 124:223-227 and 1995, *Mol. Med.* 1:821-826).

Moreover, it has been noted that in patients with respiratory conditions including *Bordetella pertussin* infection (whooping cough) and asthma, circulating γδ T cells are decreased. It has been suggested that the reason for this decrease is the dispatch of γδ T cells to the site of inflammation in the lung. (Bertotto et al., 1997, Acta Paediatr. 86:114-115; Schauer et al., 1991, Clin. Exp. Immunol. 86:440-443; Krejsek et al., 1998, Allergy 53;73-77).

Many of the studies directed to γδ T cells and airway diseases have directly suggested that γδ T cells are proinflammatory, promoting acute airway sensitization, increases in cytokine levels suggested to be involved in allergic inflammation, regulation of allergic αβ T-cell and allergen specific B-cell responses, and/or allergen-induced eosinophilia and IgE responses (e.g., McMenamin et al., 1994, *Science* 265: 1869-1871; Zuany-Amorim et al., 1998, supra; Schramm et al., 2000, *Am. J. Respir. Cell Mol. Biol.* 22:218-225; Schramm et al., 1999, International Conference of the American Thoracic Society; vol. 159:A255 (American Journal of Respiratory and Critical Care Medicine, San Diego, Calif.)). Some investigators, alternatively, have concluded that γδ T cells do not play a significant role in airway allergic inflammation. For example, Chen et al. noted, similar to other investigators discussed above, that allergic asthmatics have reduced γδ T cells in the peripheral blood. However, Chen et al. concluded that no significant correlation existed between the levels of γδ T cells and IgE present in the peripheral blood (Chen et al., 1996, *Clin. Exp. Iminunol.* 26:295-302). Although allergic asthmatics have reduced γδ T cells with reciprocally elevated eosinophil numbers in the peripheral blood, Chen et al. asserted that this does not indicate that the reduction of γδ T cells correlates with the predominance of eosinophilia or IgE levels in diseased populations. Jaffar et al. described a role for αβ, but not γδ, T cells in allergen-induced Th2 cytokine production from asthmatic bronchial tissue (Jaffar et al., 1999, *J. Immunol.* 163:6283-6291). Fajac et al., 1997, *Eur. Resp. J* 10:633-638 investigated the role of heat shock proteins and γδ T cells in patients with mild atopic asthma, and concluded that neither heat shock proteins nor γδ T cells play an important role in inflammatory and immune responses in mild asthma.

Therefore, prior to the present invention, those of skill in the art either considered γδ T cells to play an insignificant role, if any, in diseases of the airways, or believed that γδ T cells were proinflammatory cells which contributed to the development of acute airway hyperresponsiveness and other events associated with inflammation.

SUMMARY OF THE INVENTION

The present inventors have discovered that γδ cells can regulate airway function in an αβ T cell-independent manner, identifying them as important cells in pulmonary homeostasis. This function of γδ T cells differs from previously described immune-dependent mechanisms and may reflect their interaction with innate systems of host defense. Specifically, in contrast to other studies that emphasized their role in the modification of allergen-specific αβ T cell and B-cell responses, the present inventors have found that γδ T cells maintain normal airway responsiveness independently of αβ T cells.

One embodiment of the present invention relates to a method to reduce airway hyperresponsiveness in a mammal. The method includes the step of increasing γδ T cell action in a mammal that has, or is at risk of developing, a respiratory condition associated with airway hyperresponsiveness. In one aspect, the step of increasing γδ T cell action comprises increasing the number of γδ T cells in the lung tissue of the mammal. For example, the step of increasing can comprise removing γδ T cells from the mammal, inducing the γδ T cells to proliferate ex vivo to increase the number of the γδ T cells, and returning the γδ T cells to the lung tissue of the mammal. In another aspect, the step of increasing γδ T cell action comprises activating γδ T cells in the mammal. Activating γδ T cells can be performed ex vivo or in vivo.

In one embodiment of the method, the step of increasing γδ T cell action comprises administering an agent to the mammal that activates γδ T cells in the mammal. Such an agent can be any agent suitable for activating γδ T cells. In one aspect, the agent is a protein comprising a BiP-binding motif, wherein the protein is administered in an amount effective to induce proliferation of γδ T cells in the mammal. In another aspect, the agent is selected from the group consisting of a glycosylated protein and a glycosylated peptide. In another aspect, the agent is selected from the group consisting of polyGT and poly GAT (1:1:1). In yet another embodiment, the agent is selected from the group of: synthetic GC, synthetic AT and other oligonucleotides. In yet another aspect, the agent is a mycobacterial product. In another aspect, the agent is a Listeria cell wall product. In another aspect, the agent is a cardiolipin. In yet another aspect, the agent is tumor necrosis factor-α (TNF-α). In one aspect, the agent is an antibody that specifically binds to a γδ T cell receptor and activates the γδ T cells. Preferably, the agent is an antibody that specifically binds to a γδ T cell receptor (TCR) from a γδ T cell subset that is particularly suitable for regulation of airway hyperresponsiveness. Such a TCR includes, but is not limited to, a murine TCR comprising Vγ4 and a human TCR comprising Vγ1.

In one aspect of the method of the present invention, the agent is targeted to γδ T cells in the mammal. Preferably, the agent is targeted to γδ T cells in the lung tissue of the mammal. In one embodiment, the agent is targeted to γδ T cell subsets that are particularly suitable for regulation of airway hyperresponsiveness, such γδ T cells having a T cell receptor (TCR) selected from: a murine TCR comprising Vγ4 and a human TCR comprising Vγ1. In one aspect, the agent comprises: (a) an antibody that specifically binds to a molecule on the cell surface of γδ T cells; and (b) a compound that activates the γδ T cells, wherein the compound is linked to the antibody of (a). The compound can include, but is not limited to: a protein comprising a peptide having a BiP-binding motif, a glycosylated protein or peptide, polyGT, polyGAT (1:1:1), synthetic GC, synthetic AT, a mycobacterial product, a Listeria cell wall product, cardiolipin, TNF-α, and an antibody that specifically binds to a γδ T cell receptor and activates the receptor.

In one aspect of the present method, the agent is administered to the lung tissue of the mammal. In a preferred embodiment, the agent is administered by a route selected from the group consisting of inhaled, intratracheal and nasal routes. Preferably, the agent is administered to the animal in an amount effective to reduce airway hyperresponsiveness in the animal as compared to prior to administration of the agent. In one aspect, the agent is administered with a pharmaceutically acceptable excipient.

Preferably, the method of the present invention increases γδ T cell action within between about 1 hour and 6 days of an initial diagnosis of airway hyperresponsiveness in the mammal. In another embodiment, the γδ T cell action is increased within less than about 72 hours of an initial diagnosis of airway hyperresponsiveness in the mammal. In another embodiment, the γδ T cell action is increased prior to development of airway hyperresponsiveness in the mammal. Preferably, the step of increasing γδ T cell action decreases airway methacholine responsiveness in the mammal, and/or reduces airway hyperresponsiveness of the mammal such that the $FEV_1$ value of the mammal is improved by at least about 5%. It is also preferred that the step of increasing γδ T cell action improves the mammal's $PC_{20methacholin}FEV_1$ value such that the $PC_{20methacholine}FEVI_1$ value obtained before the step of increasing γδ T cell action when the mammal is provoked with a first concentration of methacholine is substantially the same as the $PC_{20methacholin}FEV_1$ value obtained after increasing γδ T cell action when the mammal is provoked with double the amount of the first concentration of methacholine. Preferably, the first concentration of methacholine is between about 0.01 mg/ml and about 8 mg/ml. The method of the present invention is suitable for treating airway hyperresponsiveness associated with any condition including, but not limited to, airway hyperresponsiveness is associated with a disease selected from the group consisting of chronic obstructive disease of the airways and asthma.

Yet another embodiment of the present invention relates to a method to identify a compound that reduces or prevents airway hyperresponsiveness associated with inflammation. The method includes the steps of: (a) contacting a putative regulatory compound with a γδ T cell; (b) detecting whether the putative regulatory compound increases the action of the γδ T cell; and, (c) administering the putative regulatory compound to a non-human animal in which airway hyperresponsiveness can be induced, and identifying animals in which airway hyperresponsiveness is reduced or prevented as compared to in the absence of the putative regulatory compound. A putative regulatory compound that increases γδ T cell action and that reduces or prevents airway hyperresponsiveness in the non-human animal is indicated to be a compound for reducing or preventing hyperresponsiveness. Preferably, step (b) of detecting is selected from the group consisting of measurement proliferation of the γδ T cell, measurement of cytokine production by the γδ T cell, measurement of calcium mobilization in the γδ T cell, measurement of cytokine receptor expression by the γδ T cell, measurement of CD69 upregulation by the γδ T cell, measurement of upregulation, of CD44 by the γδ T cell, and measurement of cytoskeletal reorganization by the γδ T cell.

BRIEF DESCRIPTION OF THE DRAWINGS

FIG. 3E is a bar graph showing BAL fluid cell composition for total cells, eosinophils and macrophages in sham-depleted TCR-$\beta^{-/-}$ mice and γδ-depleted TCR-$\beta^{-/-}$ mice after aerosol only airway sensitization.

FIG. 3F is a bar graph showing BAL fluid cell composition for total cells, eosinophils and macrophages in sham-depleted TCR-$\beta^{-/-}$ mice and αβ-depleted TCR-$\beta^{-/-}$ mice after aerosol only airway sensitization.

DETAILED DESCRIPTION OF THE INVENTION

Figure 1C:
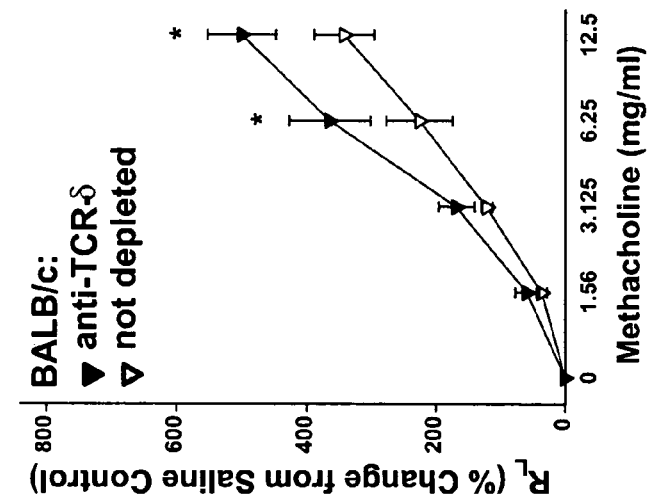
FIG. 1C is a line graph showing changes in airway resistance ($R_L$) in TCR-δ-depleted or sham-depleted BALB/c mice after systemic airway sensitization.

The present invention generally relates to a method to reduce or prevent airway hyperresponsiveness (AHR) in an animal that has, or is at risk of developing, airway hyperresponsiveness, by increasing the action of γδ T cells (i.e., γδ T lymphocytes) in the animal. In the method of the present invention, the animal has, or is at risk of developing, airway hyperresponsiveness associated with inflammation. For example, airway hyperresponsiveness is commonly associated with allergic inflammation and/or viral-induced inflammation. Airway hyperresponsiveness associated with allergic inflammation can occur in a patient that has, or is at risk of developing, a condition including, but not limited to, any chronic obstructive disease of the airways. Such conditions include, but are not limited to: asthma, chronic obstructive pulmonary disease, allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma and parasitic lung disease. Airway hyperresponsiveness associated with viral-induced inflammation can occur in a patient that has, or is at risk of developing, an infection by a virus including, but not limited to, respiratory syncytial virus (RSV), parainfluenza virus (PIV), rhinovirus (RV) and adenovirus.

The present invention is based on the present inventors' discovery that γδ T cells maintain normal airway responsiveness independently of αβ T cells and that the increased action of γδ T cells in patient's that have, or are at risk of developing, airway hyperresponsiveness will have a beneficial effect. To define the role of γδ T cells in controlling the development of AHR, the present inventors used an established mouse model of eosinophilic airway inflammation and allergen-driven alterations in airway function. The results of this research demonstrated a previously unknown, γδ T cell-dependent mechanism in the regulation of airway responsiveness which is independent of αβ T cells and their allergen-specific responses. Furthermore, the present inventors' have found no evidence to indicate that antibodies are involved in this regulatory mechanism or that changes in cytokine levels previously suggested to be involved in models allergic inflammation are involved (McMenamin et al., 1994, *Science* 265:186-1871; Zuany-Amorim et al., 1998, supra). The present inventors' discovery was surprising, because the results differ from earlier reports, which have emphasized the role of γδ T cells in regulating allergic αβ T-cell and allergen specific B-cell responses, or their role in promoting allergen-induced eosinophilia and IgE responses (McMenamin et al., 1994, supra; Zuany-Amorim et al., 1998, supra; Schramm et al., 1999, International Conference of the American Thoracic Society; vol. 159:A255 (American Journal of Respiratory and Critical Care Medicine, San Diego, Calif.)). The mechanism of γδ T cell-dependent regulation of airway responses described herein is therefore not restricted to allergic inflammation.

One embodiment of the present invention relates to a method to reduce or prevent airway hyperresponsiveness in an animal. This method includes a step of increasing γδ T cell action in a mammal that has, or is at risk of developing, a respiratory condition associated with airway hyperresponsiveness. According to the present invention, "airway hyperresponsiveness" or "AHR" refers to an abnormality of the airways that allows them to narrow too easily and/or too much in response to a stimulus capable of inducing airflow limitation. AHR can be a functional alteration of the respiratory system caused by inflammation or airway remodeling (e.g., such as by collagen deposition). Airflow limitation refers to narrowing of airways that can be irreversible or reversible. Airflow limitation and/or airway hyperresponsiveness can be caused by collagen deposition, bronchospasm, airway smooth muscle hypertrophy, airway smooth muscle contraction, mucous secretion, cellular deposits, epithelial destruction, alteration to epithelial permeability, alterations to smooth muscle function or sensitivity, abnormalities of the lung parenchyma and/or infiltrative diseases in and around the airways. Many of these causative factors can be associated with inflammation. The present invention is directed to any airway hyperresponsiveness, including airway hyperresponsiveness that is associated with inflammation of the airways, eosinophilia and inflammatory cytokine production. Methods of measuring and monitoring AHR are discussed in detail below.

As used herein, to reduce airway hyperresponsiveness refers to any measurable reduction in airway hyperresponsiveness and/or any reduction of the occurrence or frequency with which airway hypertesponsiveness occurs in a patient. A reduction in AHR can be measured using any of the above-described techniques or any other suitable method known in the art. Preferably, airway hyperresponsiveness, or the potential therefore, is reduced, optimally, to an extent that the animal no longer suffers discomfort and/or altered function resulting from or associated with airway hyperresponsiveness. To prevent airway hyperresponsiveness refers to preventing or stopping the induction of airway hyperresponsiveness before biological characteristics of airway hyperresponsiveness as discussed above can be substantially detected or measured in a patient.

AHR can be measured by a stress test that comprises measuring an animal's respiratory system function in response to a provoking agent (i.e., stimulus). AHR can be measured as a change in respiratory function from baseline plotted against the dose of a provoking agent (a procedure for such measurement and a mammal model useful therefore are described in detail below in the Examples). Respiratory function can be measured by, for example, spirometry, plethysmograph, peak flows, symptom scores, physical signs (i.e., respiratory rate), wheezing, exercise tolerance, use of rescue medication (i.e., bronchodialators) and blood gases. In humans, spirometry can be used to gauge the change in respiratory function in conjunction with a provoking agent, such as methacholine or histamine. In humans, spirometry is performed by asking a person to take a deep breath and blow, as long, as hard and as fast as possible into a gauge that measures airflow and volume. The volume of air expired in the first second is known as forced expiratory volume ($FEV_1$) and the total amount of air expired is known as the forced vital capacity (FVC). In humans, normal predicted $FEV_1$ and FVC are available and standardized according to weight, height, sex and race. An individual free of disease has an $FEV_1$ and a FVC of at least about 80% of normal predicted values for a particular person and a ratio of $FEV_1$/FVC of at least about 80%. Values are determined before (i.e, representing a mammal's resting state) and after (i.e., representing a mammal's higher lung resistance state) inhalation of the provoking agent. The position of the resulting curve indicates the sensitivity of the airways to the provoking agent.

The effect of increasing doses or concentrations of the provoking agent on lung function is determined by measuring the forced expired volume in 1 second ($FEV_1$) and $FEV_1$ over forced vital capacity ($FEV_1$/FVC ratio) of the mammal challenged with the provoking agent. In humans, the dose or concentration of a provoking agent (i.e., methacholine or histamine) that causes a 20% fall in $FEV_1$ ($PD_{20}FEV_1$) is indicative of the degree of AHR. $FEV_1$ and FVC values can be measured using methods known to those of skill in the art.

Pulmonary function measurements of airway resistance ($R_L$) and dynamic compliance ($C_{dyn}$ or $C_L$) and hyperresponsiveness can be determined by measuring transpulmonary pressure as the pressure difference between the airway opening and the body plethysmograph. Volume is the calibrated pressure change in the body plethysmograph and flow is the digital differentiation of the volume signal. Resistance ($R_L$) and compliance ($C_L$) are obtained using methods known to those of skill in the art (e.g., such as by using a recursive least squares solution of the equation of motion). The measurement of lung resistance ($R_L$) and dynamic compliance ($C_L$)

are described in detail in the Examples. It should be noted that measuring the airway resistance ($R_L$) value in a non-human mammal (e.g., a mouse) can be used to diagnose airflow obstruction similar to measuring the $FEV_1$ and/or $FEV_1/FVC$ ratio in a human.

A variety of provoking agents are useful for measuring AHR values. Suitable provoking agents include direct and indirect stimuli. Preferred provoking agents include, for example, an allergen, methacholine, a histamine, a leukotriene, saline, hyperventilation, exercise, sulfur dioxide, adenosine, propranolol, cold air, an antigen, bradykinin, acetylcholine, a prostaglandin, ozone, environmental air pollutants and mixtures thereof. Preferably, Mch is used as a provoking agent. Preferred concentrations of Mch to use in a concentration-response curve are between about 0.001 and about 100 milligram per milliliter (mg/ml). More preferred concentrations of Mch to use in a concentration-response curve are between about 0.01 and about 50 mg/ml. Even more preferred concentrations of Mch to use in a concentration-response curve are between about 0.02 and about 25 mg/ml. When Mch is used as a provoking agent, the degree of AHR is defined by the provocative concentration of Mch needed to cause a 20% drop of the $FEV_1$ of a mammal ($PC_{20methacholine}FEV_1$). For example, in humans and using standard protocols in the art, a normal person typically has a $PC_{20methacholine}FEV_1 > 8$ mg/ml of Mch. Thus, in humans, AHR is defined as $PC_{20methacholine}FEV_1 < 8$ mg/ml of Mch.

According to the present invention, respiratory function can also be evaluated with a variety of static tests that comprise measuring an animal's respiratory system function in the absence of a provoking agent. Examples of static tests include, for example, spirometry, plethysmographically, peak flows, symptom scores, physical signs (i.e., respiratory rate), wheezing, exercise tolerance, use of rescue medication (i.e., bronchodialators) and blood gases. Evaluating pulmonary function in static tests can be performed by measuring, for example, Total Lung Capacity (TLC), Thoracic Gas Volume (TgV), Functional Residual Capacity (FRC), Residual Volume (RV) and Specific Conductance (SGL) for lung volumes, Diffusing Capacity of the Lung for Carbon Monoxide (DLCO), arterial blood gases, including pH, $P_{O2}$ and $P_{CO2}$ for gas exchange. Both $FEV_1$ and $FEV_1/FVC$ can be used to measure airflow limitation. If spirometry is used in humans, the $FEV_1$ of an individual can be compared to the $FEV_1$ of predicted values. Predicted $FEV_1$ values are available for standard normograms based on the animal's age, sex, weight, height and race. A normal animal typically has an $FEV_1$ at least about 80% of the predicted $FEV_1$ for the animal. Airflow limitation results in a $FEV_1$ or FVC of less than 80% of predicted values. An alternative method to measure airflow limitation is based on the ratio of $FEV_1$ and FVC ($FEV_1/FVC$). Disease free individuals are defined as having a $FEV_1/FVC$ ratio of at least about 80%. Airflow obstruction causes the ratio of $FEV_1/FVC$ to fall to less than 80% of predicted values. Thus, an animal having airflow limitation is defined by an $FEV_1/FVC$ less than about 80%.

In one embodiment, the method of the present invention decreases methacholine responsiveness in the animal. Preferably, the method of the present invention results in an improvement in a mammal's $PC_{20methacholine}FEV_1$ value such that the $PC_{20methacholine}FEV_1$ value obtained before use of the present method when the mammal is provoked with a first concentration of methacholine is the same as the $PC_{20methacholine}FEV_1$ value obtained after use of the present method when the mammal is provoked with double the amount of the first concentration of methacholine. Preferably, the method of the present invention results in an improvement in a mammal's $PC_{20methacholine}FEV_1$ value such that the $PC_{20methacholine}FEV_1$ value obtained before the use of the present method when the animal is provoked with between about 0.01 mg/ml to about 8 mg/ml of methacholine is the same as the $PC_{20methacholine}FEV$, value obtained after the use of the present method when the animal is provoked with between about 0.02 mg/ml to about 16 mg/ml of methacholine.

In another embodiment, the method of the present invention improves an animal's $FEV_1$ by at least about 5%, and more preferably by between about 6% and about 100%, more preferably by between about 7% and about 100%, and even more preferably by between about 8% and about 100% of the mammal's predicted $FEV_1$. In another embodiment, the method of the present invention improves an animal's $FEV_1$ by at least about 5%, and preferably, at least about 10%, and even more preferably, at least about 25%, and even more preferably, at least about 50%, and even more preferably, at least about 75%.

In yet another embodiment, the method of the present invention results in an increase in the $PC_{20methacholine}FEV_1$ of an animal by about one doubling concentration towards the $PC_{20methacholine}FEV_1$ of a normal animal. A normal animal refers to an animal known not to suffer from or be susceptible to abnormal AHR. A patient, or test animal refers to an animal suspected of suffering from or being susceptible to abnormal AHR.

Therefore, an animal that has airway hyperresponsiveness is an animal in which airway hyperresponsiveness is measured or detected, such as by using one of the above methods for measuring airway hyperresponsiveness. To be associated with inflammation, the airway hyperresponsiveness is apparently or obviously, directly or indirectly associated with (e.g., caused by, a symptom of, indicative of, concurrent with) an inflammatory condition or disease (i.e., a condition or disease characterized by inflammation). Typically, such an inflammatory condition or disease is at least partially characterized by inflammation of pulmonary tissues. Such conditions or diseases are discussed above. An animal that is at risk of developing airway hyperresponsiveness can be an animal that has a condition or disease which is likely to be associated with at least a potential for airway hyperresponsiveness, but does not yet display a measurable or detectable characteristic or symptom of airway hyperresponsiveness. An animal that is at risk of developing airway hyperresponsiveness also includes an animal that is identified as being predisposed to or susceptible to such a condition or disease.

Inflammation is typically characterized by the release of inflammatory mediators (e.g., cytokines or chemokines) which recruit cells involved in inflammation to a tissue. For example, a condition or disease associated with allergic inflammation is a condition or disease in which the elicitation of one type of immune response (e.g., a Th2-type immune response) against a sensitizing agent, such as an allergen, can result in the release of inflammatory mediators that recruit cells involved in inflammation in a mammal, the presence of which can lead to tissue damage and sometimes death. Airway hyperresponsiveness associated with allergic inflammation can occur in a patient that has, or is at risk of developing, any chronic obstructive disease of the airways, including, but not limited to, asthma, chronic obstructive pulmonary disease, allergic bronchopulmonary asp ergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma and parasitic lung disease. Preferred conditions to treat using the method of the present invention include asthma, chronic obstructive disease of the airways, occupational asthma, exercise-induced asthma, pollution-induced asthma and reactive airway disease syndrome, with chronic obstructive disease of the airways and asthma being particularly preferred for treatment. Viral-induced inflammation typically involves the elicitation of another type of immune response (e.g., a Th1-type immune response) against viral antigens, resulting in production of inflammatory mediators the recruit cells involved in inflammation in a an animal, the presence of which can also lead to tissue damage. Aiiway hyperresponsiveness associated with viral-induced inflammation can occur in a patient that has, or is at risk of developing, an infection by a virus including, but not limited to, respiratory syncytial virus (RSV), parainflulenza virus (PIV), rhinovirus (RV) and adenovirus.

In order to reduce airway hypeiresponsiveness according to the method of the present invention, the action of γδ T cells is increased in an animal that has, or is at risk of developing AHR, including AHR associated with inflammation. A "γδ T cell" is a distinct lineage of T lymphocytes found in mammalian species and birds that expresses a particular antigen receptor (i.e., T cell receptor or TCR) that includes a γ chain and a δ chain. The γ and δ chains are distinguished from the α and β chains that make up the TCR of the perhaps more commonly referenced T cells known as "αβ T cells". The γδ heterodimer of the γδ T cells is expressed on the surface of the T cell and, like the αβ heterodimer of αβ T cells, is associated with the CD3 complex on the cell surface. The γ and δ chains of the γδ T cell receptor should not be confused with the γ and δ chains of the CD3 complex. According to the present invention, the terms "T lymphocyte" and "T cell" can be used interchangeably herein.

According to the present invention, to increase the action of γδ T cells in an animal refers to any treatment or manipulation of the animal, or specifically, of γδ T cells, which results in a detectable (e.g., measurable) increase (i.e., enhancement, upregulation, induction, stimulation) in the number, activation, biological activity and/or survivability of the γδ T cells. Therefore, increasing the action of γδ T cells according to the present invention can be accomplished by increasing the number of γδ T cells in an animal (i.e., by causing the cells to proliferate/expand or by recruiting additional γδ T cells to a site), by increasing the activation of γδ T cells in an animal, by increasing biological activity of γδ T cells (e.g., effector functions or other activities of the cell) in an animal and/or by increasing the ability of γδ T cells to survive (i.e., resist apoptosis) in an animal. According to the present invention, to increase the action of γδ T cells in an animal further refers to a step of directly acting on γδ T cells in the animal. In other words, the method of increasing the action of γδ T cells directly expands, recruits, activates, or enhances survival of γδ T cells, even though other cell types might be affected by the method, but such step is not intended to be merely a downstream result of a direct action on another cell type. Preferably, and particularly when the method is performed in vivo, the step of increasing the action of γδ T cells does not substantially directly affect (i.e., act on) other cells, such as αβ T cells, B cells, macrophages, or monocytes. In this case, selective or targeted methods for increasing γδ T cells are preferred. The increased action of γδ T cells can subsequently affect other cells, however, such as alveolar macrophages, airway epithelial and airway smooth muscle cells (i.e., increased numbers and/or activity of γδ T cells can influence the activity of other cells). It will be appreciated by those of skill in the art that when the step of increasing the action of γδ T cells is performed ex vivo or in vitro, the step of increasing γδ T cell action does not necessarily have to be selective for or targeted to γδ T cells, but preferably, γδ T cells are subsequently isolated and/or preferentially returned to the animal. Therefore, in the preferred embodiment, the method of the present invention is intended to be selective for or specifically targeted to γδ T cell activity, and in one embodiment, excludes methods which indiscriminately activate other immune system cells and/or other cell types, as well as methods which modulate γδ T cell activity as a downstream result of a direct action on another cell type.

More specifically, in one embodiment, an increase in γδ T cell action is defined herein as any detectable increase in the number of γδ T cells in a population (clonal or non-clonal) of γδ T cells. According to the present invention, an increase in the number of γδ T cells at a given site can be accomplished by: (1) causing a given population of γδ T cells to proliferate and expand; (2) inducing recruitment of additional γδ T cells to a given site, such that the total number of γδ T cells increases; and/or (3) adding additional γδ T cells to a population of T cells (e.g., T cell transfer). An increase in the number of γδ T cells is typically evaluated by measuring proliferation of γδ T cells, for example, by using a standard T cell proliferation assay (e.g., uptake of [$^3$H]-thymidine). T cell proliferation assays, including those using γδ T cells, are well known in the art, and are described, for example, in several publications by certain of the present inventors (e.g., Born et al., 1990, *Science* 249:67; O'Brien et al., 1992, *Proc. Natl. Acad. Sci. USA* 89:4348; Lahn et al., 1998, *J. Immunol.* 160:5221; Cady et al., 2000, *J. Immunol.* 165:1790; all incorporated herein by reference in their entireties). Other methods for determining an increase in the number of γδ T cells can be evaluated by detecting or measuring the expression level, and/or the distribution of γ-chain usage and/or δ chain usage in the receptors of a population of γδ T cells and determining whether there is a change in the expression level and/or distribution of one or more γδ T cell receptor types in the population. Such assays, including both molecular and flow cytometric methods, and the reagents (e.g., antibodies, hybridization probes and PCR primers specific for various γδ TCR chains) for performing such assays, are known in the art (e.g., O'Brien et al., 1992, supra; Lahn et al., 1998, supra; Cady et al., 2000, supra).

In another embodiment, an increase in γδ T cell action is any detectable increase in the activation state and/or biological activity of γδ T cells in an animal. As used herein, activation, or responsiveness, of a γδ T cell refers to the ability of a γδ T cell to be activated by (e.g., respond to) antigenic and/or mitogenic stimuli which results in induction of γδ T cell activation signal transduction pathways and activation events. The biological activity of a γδ T cell refers to any function(s) exhibited or performed by a naturally occurring γδ T cell as measured or observed in vivo (i.e., in the natural physiological environment of the cell) or in vitro (i.e., under laboratory conditions). As used herein, antigenic stimulation is stimulation of a γδ T cell by binding of the γδ T cell receptor to an antigen that is specifically recognized by the γδ T cell in the context of appropriate costimulatory signals necessary to achieve γδ T cell activation. Mitogenic stimulation is defined herein as any non-antigen stimulation of T cell activation, including by mitogens (lipopolysaccharides (LPS), phorbol esters, ionomycin) and antibodies (anti-TCR, anti-CD3, including divalent and tetravalent antibodies). Both antigenic stimulation and the forms of mitogenic stimulation which act at the level of the T cell receptor (i.e., anti-TcR/CD3) result in T cell receptor-mediated activation, whereas LPS/phorbol ester/ionomycin mitogenic stimulation bypasses the T cell receptor and therefore, do not induce T cell receptor-mediated activation, but nonetheless, can induce at least some of the downstream events of T cell activation.

Therefore, events associated with T cell activation or biological activity include, but are not limited to, T cell proliferation, cytokine production (e.g., interleukin-2 (IL-2), IL-4, IL-5, IL-10, interferon-γ (IFN-γ), tumor necrosis factor-α (TNF-α)), upregulation of cytokine receptors (e.g., IL-2 receptor, TNF-α receptor), calcium mobilization, upregulation of cell surface molecules associated with T cell activation (e.g., CD44, CD69), upregulation of expression and activity of signal transduction proteins associated with T cell activation, chemokine production, altered T cell migration, accumulation of T cells at specific tissue sites and/or cytoskeletal reorganization. The ability of a T lymphocyte to respond, or become activated, by an antigenic or mitogenic stimulus can be measured by any suitable method of measuring T cell activation. Such methods are well known to those of skill in the art. For example, after a T cell has been stimulated with an antigenmc or mitogenic stimulus, characteristics of T cell activation can be determined by a method including, but not limited to: measuring cytokine production by the T cell (e.g., by immunoassay or biological assay); measuring intracellular and/or extracellular calcium mobilization (e.g., by calcium mobilization assays); measuring T cell proliferation (e.g., by proliferation assays such as radioisotope incorporation); measuring upregulation of cytokine receptors on the T cell surface, including IL-2R (e.g., by flow cytometry, immunofluorescence assays, immunoblots, RNA assays); measuring upregulation of other receptors associated with T cell activation on the T cell surface (e.g., by flow cytometry, immunofluorescence assays, immunoblots, RNA assays); measuring reorganization of the cytoskeleton (e.g., by immunofluorescence assays, immunoprecipitation, immunoblots); measuring upregulation of expression and activity of signal transduction proteins associated with T cell activation (e.g., by kinase assays, phosphorylation assays, immunoblots, RNA assays); and, measuring specific effector functions of the T cell (e.g., by proliferation assays). Methods for performing each of these measurements are well known to those of ordinary skill in the art, many are described in detail or by reference to publications herein, and all such methods are encompassed by the present invention.

In another embodiment, an increase in γδ T cell action results in an increase in the survival of the γδ T cell (i.e., prevention or inhibition of apoptosis). According to the present invention, the present method preferably results in a measurable maintenance of γδ T lymphocyte survival (e.g., less than about 50%, and more preferably, less than about 25%, and more preferably, less than about 10%, and even more preferably, less than about 5% loss in blood γδ T lymphocyte number after employing the present method as compared to in the absence of the present method). T lymphocyte survival can be determined by measuring any of the parameters described above for measuring T cell proliferation/numbers or activation (as an indicator of responsive T cells), or by any suitable means of measuring T cell apoptosis (i.e., a reduction in γδ T cell apoptosis is indicative of enhanced γδ T cell survival). Methods of measuring apoptosis in a T cell include, but are not limited to: determining the extent of a morphological change in a cell; determining the extent of DNA cleavage by gel electrophoresis, cell cycle analysis, or in situ tailing or nick translation; assessing membrane permeability by using dyes that bind RNA or DNA or Annexin V. Such methods are well known in the art.

According to the present invention, the method for regulating airway hyperresponsiveness can be directed to any γδ T cell, wherein an increase in the action of such γδ T cell results in a decrease in airway hyperresponsiveness. Preferred γδ T cells to activate and/or expand (i.e., proliferate, increase the numbers) are γδ T cells in the lung tissue of an animal. Such γδ T cells include γδ T cells that normally reside in the lung tissue, as well as γδ T cells that are recruited into the lung upon development of a condition associated with airway hyperresponsiveness and/or upon stimulation of γδ T cells that normally reside in the lung tissue. Preferably, the present method includes a step of increasing γδ T cell action in γδ T cells that normally reside in the lung tissue.

In another preferred embodiment, the method for regulation of airway hyperresponsiveness of the present invention is directed to γδ T cells that are identified as being particularly useful for regulating AHR in an animal, wherein increased action of γδ T cells that do not regulate AHR, or which are proinflammatory (i.e., contribute to AHR), is avoided. In one aspect, a preferred γδ T cell for which increasing the action is believed to be particularly effective for reducing AHR has a T cell receptor (TCR) that comprises a Vγ4 chain (i.e., the variable (V) region of the γ chain is has a particular sequence which is known in the art as Vγ4, following the nomenclature of Tonegawa et al., for example), or the human equivalent thereof, which is believed to include Vδ1 T cells (i.e., Vγ4 is the murine cell subset). Preferably, γδ T cells having TCRs with Vγ4 chains, or the human equivalent (e.g., Vδ1), are targeted by the method of the present method. This subset of γδ T cells can be targeted, for example, by using a targeting moiety that selectively recognizes the Vγ4 chain of the TCR (e.g., an antibody that selectively binds to Vγ4) (or the Vb 1 chain of the TCR in humans, for example), or by removing cells from the lung tissue (or other tissues) and isolating γδ T cells expressing Vγ4 (or human equivalent) ex vivo.

In yet another preferred embodiment, γδ T cells that are CD8$^+$ (i.e., which express CD8) are preferred targets for the method of the present invention. Even more preferably, γδ T cells which express an αβ heterodimer of CD8 are preferably selectively targeted for activation and/or expansion according to the present method. CD8 is a costimulatory molecule expressed by subsets of both αβ T lymphocytes and γδ T lymphocytes. The CD8 molecule comprises two chains which can occur in the form of either a dimer of CD8α chains (i.e., a CD8α homodimer) or a dimer of a CD8α chain and a CD8β chain (i.e., a CD8 at heterodimer). In αβ T cells, the CD8 molecule is typically expressed as a CD8 αβ heterodimer. In contrast, in γδ T cells, the CD8 molecule is typically expressed as a CD8 α homodimer. However, the present inventors have found that a subset of γδ T cells in the lung expresses CD8 as a CD8 αβ heterodimer. Moreover, the present inventors have found that a subset of Vγ4$^+$ T cells in the murine lung express the CD8 αβ heterodimer. Without being bound by theory, the present inventors believe that γδ T cells expressing a CD8 αβ heterodimer, and particularly γδ T cells expressing Vγ4 (or the human equivalent such as V81) and a CD8 αβ heterodimer, are particularly suitable targets for the method of the present invention and are likely to be at least one primary regulatory γδ T cell subset that contributes to the reduction of AHR in vivo.

In another embodiment of the present invention, the method for regulation of ainvay hyperresponsiveness of the present invention is further directed to the inhibition of γδ T cells that are identified as being particularly enhancing of AHR in an animal, wherein decreased action of these γδ T cells that do not control AHR, and/or which are proinflammatory (i.e., contribute to AHR), is the goal. Without being bound by theory, the present inventors believe that certain subsets of γδ T cells appear to be enhancing of AHR and therefore, their targeted ablation would be beneficial in the treatment of AER. In particular, the present inventors have discovered that γδ T cells bearing a T cell receptor comprising a Vγ1 chain for murine cells (or the human equivalent, such as Vγ9NV52 expressing cells), which appear later than the regulatory Vγ1 subset discussed above, may enhance AHR. More specifically, it is believed that the CD4$^+$ Vγ1$^+$ γδ T cell subset (or the human equivalent thereof) is a particularly desirable target for inhibition by the method of the present invention. Therefore, in one embodiment of the present invention, either alone or in combination with the stimulation of Vγ4+T cells (or the human equivalent thereof) according to the present method, Vγ1$^+$ T cells (or the human equivalent thereof) are inhibited. Methods for inhibition will be clear to those of skill in the art and include, but are not limited to targeted destruction of Vγ1$^+$ T cells (or the human equivalent thereof) (e.g., by neutralizing antibodies, induced apoptosis), blocking of such TCRs by blocking antibodies (i.e., that do not stimulate the T cell), anti-sense therapy, and other such methods.

It is to be understood, however, that it is not necessary to selectively target a particular subset of γδ T cells to reduce AHR in an animal, as methods of increasing the action of γδ T cells which do not selectively target a particular subset are also effective for reducing AHR. For example, in one embodiment, γδ T cell activation that is effective for reducing AHR can be selectively targeted or enhanced by increasing γδ T cell action relatively early after airw % ay hyperresponsiveness (or initial antigen sensitization leading to AHR) is induced. Without being bound by theory, the present inventors believe that the γδ T cell responses which are effective to downregulate AHR are most effective within between about 1 hour to about 6 days after AHR is induced, and most preferably, within less than about 72 hours after AHR is induced. As discussed above, it is further believed that γδ T cells which may enhance AIHR appear later in the response, and could be avoided by early targeting, or actively ablated by later targeted delivery of γδ T cell inhibitors. Alternatively, by selectively targeting γδ T cells expressing Vγ4 (or the human equivalent thereof), the timing of the treatment may be effective at later timepoints. Other methods for directing the method of the present invention to γδ T cells, including to specific subsets of γδ T cells are discussed below.

Accordingly, the method of the present invention can be carried out by any suitable process of increasing the numbers, activation or biological activity, or survival of γδ T ciells, wherein increased action of γδ T cells is effective to reduce airway hyperresponsiveness in a mammal. Such a process can be performed in vivo, such as by administration of a compound to an animal which increases the action of γδ T cells in the animal or by transferring γδ T cells into an animal from another source. Alternatively, such a process can be performed ex vivo, such as by removing a sample of cells, tissues or bodily fluids from an any suitable tissue or region in an animal which includes γδ T cells; expanding, activating and/or selecting (isolating) γδ T cells in vitro to increase the number and/or action of γδ T cells in the sample; and returning at least the γδ T cells to the lung tissue of the animal.

In one embodiment, the method of the present invention includes the use of a variety of agents (i.e., regulatory compounds) which, by acting on γδ T cells, increase the proliferation, activationibiological activity, and/or survival of γδ T cells in the lung tissue of an animal, and/or the recruitment of other regulatory γδ T cells to the lung tissue of the animal, such that airway hyperresponsiveness is reduced in the animal. Such agents are generally referred to herein as γδ T cell agonists. According to the present invention, a γδ T cell agonist is any agent which increases, typically by direct action on the cell, the proliferation, activationibiological activity, and/or survival of γδ T cells, and includes agents which act directly on the γδ T cell receptor. A γδ T cell agonist, as referred to herein, can further include, for example, compounds that are products of rational drug design, natural products, and compounds having partially or fully defined γδ T cell stimulatory properties. A γδ T cell agonist can be a protein-based compound, a carbohydrate-based compound, a lipid-based compound, a nucleic acid-based compound, a natural organic compound, a synthetically derived organic compound, an antibody, or fragments thereof. A variety of known γδ T cell agonists are described below and all are encompassed by the present invention.

In one embodiment, γδ T cells are selectively stimulated by random heterocopolymers of glutamic acid and tyrosine, generally referred to herein as polyGT. polyGT is most commonly known as a randomly synthesized heterocopolymeric peptide composed of glutamic acid and tyrosine, with an average length of 100 amino acids and a capacity to elicit strong immune responses in certain mouse strains. As described in detail in Cady et al. (2000, *J Immunol.* 165: 1790), polyGT stimulates polyclonal proliferation of normal (e.g., splenic) γδ T cells as well as hybridomas, but not αβ cells. Therefore, polyGT is useful for selectively stimulating γδ T cells in the absence of stimulating αβ T cells, and in the absence of additional targeting of the polyGT to γδ T cells. According to the present invention, polyGT can be provided as a synthetic peptide, such as polyGlu$^{50}$Tyr$^{50}$ (publicly available from Sigma, P-0151), as a random heterocopolymer of glutamic acid and tyrosine of any other length which is sufficient to elicit a γδ T cell response (i.e., stimulation, activation), and by several natural proteins which contain such repeats, including predicted and actual proteins in bacteria, viruses, mice and humans. Such sequences, and the proteins containing such sequences, can be readily identified by performing simple sequence searches in the public sequence databases. Such peptides are simple to produce and test for γδ T cell stimulation, using methods formeasuring γδ T cell stimulation as described elsewhere herein and in Cady et al., ibid., which is incorporated herein by reference in its entirety.

In another embodiment, a peptide referred to a polyGAT (1:1:1) is also stimulatory for γδ T cells and can be used in the present method. PolyGAT is a synthetic peptide that is comprised of glutamic acid, alanine and tyrosine in a 1:1:1 ratio. The peptide was named prior to the now universally standard single letter code for amino acids.

Yet another γδ T cell agonist includes synthetic AT and other oligonucleotides (i.e., nucleic acid sequences having from about 5 to about 100 nucleotides, and more preferably from about 5 to about 50, and more preferably from about 5 to about 30 nucleotides). Synthetic AT is an oligonucleotide of at least 5 nucleotides composed of adenosine and tbymidine. Other types of oligonucleotides, including those composed of guanine and cytosine, are also stimulatory for γδ T cells. Shorter oligonucleotides (less than 20 nucleotides) stimulate only when immobilized (e.g., on any suitable substrate) or otherwise polymerized.

In one embodiment of the present invention, the agent used for increasing γδ T cell action is an antibody. In one aspect, the antibody selectively binds to a γδ T cell in a manner such that the γδ T cell proliferation, survival or activation is increased. In a preferred aspect, the antibody selectively binds to the γδ T cell receptor (γδ TCR) and activates the γδ T cell by such binding. In one aspect, the antibody selectively binds to a specific subset of γδ T cell receptors which are identified as being particularly effective to reduce airway hyperresponsiveness in an animal. In a particularly preferred embodiment, the antibody binds to a γδ T cell receptor expressing a Vγ4 chain. As used herein, the term "selectively binds to" refers to the ability of antibodies of the present invention to preferentially bind to specified proteins (e.g., a γδ T cell receptor). Binding can be measured using a variety of methods standard in the art including enzyme immunoassays (e.g., ELISA), immunoblot assays, radioimmunoassays, etc. Several antibodies which selectively bind to a γδ T cell receptor are known in the art and are publicly available. Such antibodies include, but are not limited to: anti-TCR-δ (GL3, GL4 and $UC_{7-13}D5$ (PharMingen, San Diego, Calif.); or 403.A10); anti-mouse TCR-Vγ1 (2.11); anti-TCR-Vγ4 ($UC_{3-10}A6$; PharMingen, San Diego, Calif.). Isolated antibodies of the present invention can include serum containing such antibodies, or antibodies that have been purified to varying degrees. Antibodies of the present invention can be polyclonal or monoclonal, functional equivalents such as antibody fragments (e.g., Fab fragments or $Fab_2$ fragments) and genetically-engineered antibodies, including single chain antibodies or chimeric antibodies, including bi-specific antibodies that can bind to more than one epitope.

Generally, in the production of an antibody, a suitable experimental animal, such as a rabbit, hamster, guinea pig or mouse, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies. Such serum is useful as a reagent. Polyclonal antibodies can be further purified from the serum by, for example, treating the serum with ammonium sulfate. In order to obtain monoclonal antibodies, the immunized animal is sacrificed and B lymphocytes are recovered from the spleen. The differentiating and proliferating daughter cells of the B lymphocytes are then fused with rmyeloma cells to obtain a population of hybridoma cells capable of continual growth in suitable culture medium. Hybridomas producing a desired antibody are selected by testing the ability of an antibody produced by a hybridoma to bind to the antigen. Methods of producing both polyclonal and monoclonal antibodies of a desired specificity are well known in the art.

Another agent that is particularly useful for increasing the action of γδ T cells includes a protein or peptide having a corresponding to a consensus motif that has been identified as being bound by the molecular chaperone known as BiP. This consensus motif is described in detail in Blond-Elguindi et al., 1993, *Cell* 75:717-728, incorporated herein by reference in its entirety. More particularly, the molecular chaperone, BiP, is the sole member of the HSP70 family localized in the endoplasmic reticulum. BiP is required for translocation fo newly synthesized proteins across the ER membrane and for their subsequent folding and assembly in the ER lumen. The role of BiP as chaperone depends on its ability to recognize a wide variety of nascent polypeptides that share no obvious sequence similarity, while discriminating between properly folded and unfolded structures. Blond-Elguindi et al. identified a heptameric consensus motif shared by peptides bound by BiP which can be used to predict and identify BiP-binding sites in natural proteins. It is the peptides consisting essentially of these BiP-binding sites, including such peptides found in various mycobacteria and bacteria, which, without being bound by theory, the present inventors believe may be particularly stimulatory for γδ T cells. As set forth in Blond-Elguindi, the BiP binding motif is best set forth as Hy(W/X)HyXHyXHy, where Hy is a large hydrophobic amino acid (most frequently Trp, Leu or Phe), W is Trp, and X is any amino acid. This core motif is of the size determined previously to fill the peptide-binding pocket of BiP (Flynn et al., 1991, *Science* 245:385). Additionally, the following amino acid tendencies at various positions have been observed: Gln is enriched at positions 4 and 8; Met, Gly and Thr are enriched at position 3; Asn, Ser and Tyr are enriched at position 5; and His, Ile, Pro and Thr are enriched at position 7. The present inventors have found that several peptides having this motif are capable of stimulating γδ T cell responses. Such peptides include the peptide identified by SEQ ID NO:1 which has the amino acid sequence denoted FALQLEL. This sequence is an artificial sequence that the present inventors have modified from a mycobacterial HSP-60 protein (from *M. leprae*) (i.e., FGLQLEL, SEQ ID NO:2), both of which the present inventors have identified as being stimulatory for γδ T cells. SEQ ID NO:1 was generated by the present inventors to better stimulate γδ T cell hybridomas (Fu et al., 1994, *J. Immunol.* 152:1578). Additional peptides having the BiP binding motif from other organisms, including other mycobacteria, bacteria, yeast, and mammals (human and mouse) have proven to be stimulatory for γδ T cells (data not shown herein). Such peptides, and proteins comprising such peptides in a form which is accessible to the γδ T cell receptor, are encompassed by the present invention for use in increasing the action of γδ T cells.

According to the present invention, peptides suitable for stimulation of γδ T cells are at least about seven amino acids in length, and can include peptides of at least about 8, 9, 10, 11, 12, 13, 14, 15, 16, 17, 18, 19, or 20 amino acids. In one embodiment, a stimulatory consisting essentially of a given specified peptide (i.e., a peptide having the BiP peptide-binding motif) can include up to about 10 additional amino acids on either side of the BiP-binding motif. A protein comprising a suitable yoT cell stimulatory peptide is not restricted in size, but must have the ability to increase γδ T cell action as described herein.

Yet another agent that is useful for increasing the action of γδ T cells according to the present invention is tumor necrosis factor-α (TNF-α). The present inventors have previously described that TNF-α is a particularly effective mediator of γδ T cell activation (See Lahn et al., 1998, supra). Specifically, investigating very early T cell activation in mouse and human models of bacterial infection, the present inventors measured early cellular activation of T cells and found that, while both murine αβ and γδ T cells responded polyclonally to systemic bacterial infections and to lipopolysaccharides (LPS), γδ T cells responded more strongly to the bacteria and to LPS. The present inventors then identified tumor necrosis factor α (TNF-α) as the mediator of the early differential T cell activation, and of differential proliferative responses. The stronger response of γδ T cells to TNF-α was correlated with higher expression levels of TNF-Rp75, suggesting that this TNF-R determines the differential T cell reactivity. These data indicated that TNF-α is an early preferential activator of γδ T cells, connecting γδ T cell functions with those of cells that produce this cytokine, including activated innate effector cells and antigen-stimulated T lymphocytes. Now, the present inventors have additionally demonstrated that TNF-α negatively modulates (i.e., reduces or controls) airway hyperresponsiveness by activating γδ T cells. These results are described in detail in Example 6. Therefore, one embodiment of the present invention comprises increasing the action of γδ T cells in an animal by administering to the animal TNF-α. In one embodiment, the TNF-α is administered to the lung tissue of an animal. In a preferred embodiment, the TNF-α is targeted to γδ T cells in vivo or ex vivo by one of the methods of selectively targeting γδ T cells as described elsewhere herein.

Other agents useful for increasing the action of γδ T cells include various compounds that can be associated with bacteria and/or viruses. Such compounds include, but are not limited to: glycosylated proteins or peptides, mycobacterial products, and Listeria cell wall products. It is known that γδ T cells respond during bacterial and viral infections. Additionally, in two mouse models of infection with the facultative intracellular bacterium *Listeria monocytogenes*, depletion of γδ T cells resulted in prolonged and exacerbated inflammation of the target organs, which underwent extensive tissue destruction (Fu et al., supra; Mombaerts et al., 1993, *Nature* 365:53; Mukasa et al., 1995, *J Immunol.* 155:2047). Depletion of αβ T cells did not have the same consequences, despite comparable or increased bacterial loads. Similar findings were also recently reported in a mouse model of lung infection with *Mycobacterium tuberculosis* (D'Souza et al., 1997, *J Jmmunol.* 158:1217). It has not been resolved whether γδ T cell reactivity in these infections is directly dependent on antigen recognition by these cells, or instead is merely driven by the innate and adaptive host responses to the bacteria, although stimulation of γδ T cells by bacterial components has been well documented (Haas et al., 1993, *Annu. Rev. Immunol.* 11:637). Particularly strong γδ T cell responses have been noted after infection of mice with certain Gram-negative bacteria, including *Escherichia coli* and *Salmonella* strains (Takad a et al., 1993, *J. Immunol.* 151:2062; Emoto et al., 1992, *J. Exp. Med.* 176:363; Mixter et al., 1994, *Infect. Immun.* 62:4618). Although it is controversial whether γδ T cells contribute to host protection against these pathogens (Weintraub et al., 1997, *Infect. Immun.* 65:2306), it has been demonstrated that γδ T cells can be stimulated by lipopolysaccharides (LPS) (Skeen et al., 1993, *J. Exp. Med.* 178:971; Reardon et al., 1995, *J. Invest. Dermatol.* 105:585; Tsuji et al., 1996, *Int. Immunol.* 8:359). The present inventors have recently found that γδ T cells responded more strongly to two types of systemic bacterial infection and to LPS than did ad T cells (Lahn et al., 1998, *J. Immunol.* 160:5221). Finally, the present inventors have also previously demonstrated that γδ T cell hybridomas respond in vitro to mycobacterial proteins, including portions of the mycobacterial heat shock protein HSP65. Without being bound by theory, the present inventors believe that the activation of γδ T cells by this protein may be related to the presence of a BiP-binding motif as discussed above. To the extent that portions (i.e., peptides) of the mycobacterial heat shock proteins, and particularly, portions of the mycobacterial HSP-60 family proteins, stimulate γδ T cells and through this action reduce AHR, such proteins or the portions thereof are encompassed as useful agents by the present invention.

In another embodiment, γδ T cell agonists can include cardiolipin. Cardiolipin is a phospholipid that selectively stimulates γδ T cell hybridomas but not αβ T cell hybridomas. Most other phospholipids tested by the present inventors have not been stimulatory, although phosphatidyl-glycerol is weakly stimulatory and therefore, this phospholipid, or an improved homologue thereof, may also be useful in the present invention.

For the activation of γδ T cells, the present invention also includes the use of "phosphoantigens". Phosphoantigens are antigens containing phosphate groups such as isoprenylpyrophosphate (IPP) and many others that have been characterized by the research groups of Michael Brenner and others (e.g., Tanaka et al., 1995, *Nature* 375:155-158). Yet another γδ T cell stimulatory agent includes carbin alkylamines, including those that are present in microbes, edible plants and Tea (Bukowski et al., 1999, *Immunity* 11:57-65).

In one embodiment, γδ T cell agonists of the present invention include products of drug design, including peptides, oligonucleotides, carbohydrates and/or synthetic organic molecules which regulate the proliferation, activation/biological activity, and/or survival of γδ T cells. Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, *Molecular Biotechnology: Therapeutic Applications and Strategies*, Wiley-Liss, Inc., which is incorporated herein by reference in its entirety. Candidate compounds initially identified by drug design methods can be screened for γδ T cell stimulatory activity and an ability to reduce AHR by increasing the action of γδ T cells using the methods described elsewhere herein.

In a molecular diversity strategy, large compound libraries are synthesized, for example; from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., supra.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Various other methods of structure-based drug design are disclosed in Maulik et al., 1997, supra. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In one embodiment, additional regulators γδ T cells can be identified by using high-throughput screening methods, including DNA arrays.

In accordance with the present invention, acceptable protocols to administer an agent (i.e., an agent/compound that increases γδ T cell activation), including the route of administration and the effective amount of an agent to be administered to an animal, can be determined and accomplished by those skilled in the art. An agent of the present invention can be administered in vivo or ex vivo. Suitable in vivo routes of administration can include, but are not limited to, oral, nasal, inhaled, topical, intratracheal, transdenial, rectal, and parenteral routes. Preferred parenteral routes can include, but are not limited to, subcutaneous, intradermal, intravenous, intramuscular, and intraperitoneal routes. Preferred topical routes include inhalation by aerosol (i.e., spraying) or topical surface administration to the skin of a mammal. Most preferably, an agent is administered to the lung tissue of an animal. Routes suitable for delivery of an agent to the lung tissue include, but are not limited to: nasal, inhaled, intratracheal, or intravenous routes. Most preferably, an agent is administered to an animal by nasal, inhaled, or intratracheal routes.

Ex vivo refers to performing part of the administration step outside of the patient, such as by removing cells from a patient, culturing such cells in vitro to increase γδ T cell action, and returning the cells, or a subset thereof (e.g., isolated γδ T cells) to the patient. Ex vivo methods are particularly useful because the γδ T cells in the lung of the patient can be isolated from other cells in vitro, and expanded/activated prior to return of the cells to the lung of the patient. Therefore, it is not necessary to specifically isolate γδ T cells from a patient, but rather, a tissue, cell population and/or bodily fluid containing γδ T cells can be initially isolated, followed by stimulation of the cells by yb-specific or non-specific methods of T cell stimulation. Either prior to or subsequent to such stimulation, if desired, the γδ T cells can be isolated for return to the patient as a substantially homogeneous γδ T cell population in which γδ T cell action has been increased. It is noted, however, that separation of the γδ T cells from the other cells removed from the patient is not required and in some circumstances, may not be desirable (e.g., other cells removed from the patient might be valuable as being positively affected by γδ T cell activation). In this instance, γδ T cells can be selectively activated and/or expanded ex vivo, and returned to the patient with the other cells.

Preferably, in an ex vivo method, the sample containing the γδ T cells to be manipulated is obtained from the lung tissue of the patient. Methods for obtaining cells from and returning cells to the lung of an animal, including bronchoalveolar lavage, are well known in the art. In addition, as described above, methods for manipulating γδ T cells ex vivo (i.e., iii vitro) are also well known in the art.

According to the method of the present invention, an effective amount of a agent that increases γδ T cell action (also referred to simply as "an agent") to administer to an animal comprises an amount that is capable of reducing airway hyperresponsiveness (AHR) without being toxic to the mammal. An amount that is toxic to an animal comprises any amount that causes damage to the structure or function of an animal (i.e., poisonous).

In one embodiment, the effectiveness of an agent that increases γδ T cell action to protect an animal from AHR in an animal having or at risk of developing AHR can be measured in doubling amounts. For example, the ability of an animal to be protected from AHR (i.e., experience a reduction in or a prevention of) by administration of a given γδ T cell agonist is significant if the animal's $PC_{20methacholine}FEV_1$ is at 1 mg/ml before administration of the γδ T cell agonist and is at 2 mg/ml of Mch after administration of the γδ T cell agonist. Similarly, a γδ T cell agonist is considered to be effective if the animal's $PC_{20methacholine}FEV_1$ is at 2 mg/ml before administration of the γδ T cell agonist, and is at 4 mg/ml of Mch after administration of the γδ T cell agonist. Methods for measuring an animal's $PC_{20methacholine}FEV_1$ have been described above and are well known in the art.

In one embodiment of the present invention; in an animal that has AHR, an effective amount of an agent to administer to an animal is an amount that measurably reduces AHR in the animal as compared to prior to administration of the agent. In another embodiment, an effective amount of an agent to administer to an animal is an amount that measurably reduces AHR in the animal as compared to a level of airway AJR in a population of animals with inflammation that is associated with AHR wherein the agent was not administered.

In one embodiment of the present invention, an effective amount of an agent to administer to an animal includes an amount that is capable of decreasing methacholine responsiveness without being toxic to the animal. A preferred effective amount of an agent comprises an amount that is capable of increasing the $PC_{20methacholine}FEV_1$ of an animal treated with the an agent by about one doubling concentration towards the $PC_{20methacholine}FEV_1$ of a is normal animal. A normal animal refers to an animal known not to suffer from or be susceptible to abnormal AHR. A test animal refers to an animal suspected of suffering from or being susceptible to abnormal AHR.

In another embodiment, an effective amount of an agent according to the method of the present invention, comprises an amount that results in an improvement in an animal's $PC_{20methacholine}FEV_1$ value such that the $PC_{20methacholine}FEV_1$ value obtained before administration of the an agent when the animal is provoked with a first concentration of methacholine is the same as the $PC_{20methacholine}FEV_1$ value obtained after administration of the an agent when the animal is provoked with double the amount of the first concentration of methacholine. A preferred amount of an agent comprises an amount that results in an improvement in an animal's $PC_{20methacholine}FEV_1$ value such that the $PC_{20methacholine}FEV_1$ value obtained before administration of the an agent is between about 0.01 mg/ml to about 8 mg/ml of methacholine is the same as the $PC_{20methacholine}FEV_1$ value obtained after administration of the an agent is between about 0.02 mg/ml to about 16 mg/ml of methacholine.

As previously described herein, the effectiveness of an agent to protect an animal having or susceptible to AHR can be determined by measuring the percent improvement in $FEV_1$ and/or the $FEV_1/FVC$ ratio before and after administration of the agent. In one embodiment, an effective amount of an agent comprises an amount that is capable of reducing the airflow limitation of an animal such that the $FEV_1/FVC$ value of the animal is at least about 80%. In another embodiment, an effective amount of an agent comprises an amount that is capable of reducing the airflow limitation of an animal such that the $FEV_1/FVC$ value of the animal is improved by at least about 5%, or at least about 100 cc or PGFRG 10 L/min. In another embodiment, an effective amount of an agent comprises an amount that improves an animal's $FEV_1$ by at least about 5%, and more preferably by between about 6% and about 100%, more preferably by between about 7% and about 100%, and even more preferably by between about 8% and about 100% (or about 200 ml) of the animal's predicted $FEV_1$. In another embodiment, an effective amount of an agent comprises an amount that improves an animal's $FEV_1$ by at least about 5%, and preferably, at least about 10%, and even more preferably, at least about 25%, and even more preferably, at least about 50%, and even more preferably, at least about 75%.

It is within the scope of the present invention that a static test can be performed before or after administration of a provocative agent used in a stress test. Static tests have been discussed in detail above.

A suitable single dose of an agent that increases γδ T cell action (i.e., a γδ T cell agonist) to administer to an animal is a dose that is capable of reducing or preventing airway hyperresponsiveness in an animal when administered one or more times over a suitable time period. In particular, a suitable single dose of an agent comprises a dose that improves AHR by a doubling dose of a provoking agent or improves the static respiratory function of an animal. A preferred single dose of an agent typically comprises between about 0.01 microgram× kilogram$^{-1}$ and about 10 milligram×kilogram$^{-1}$ body weight of an animal. A more preferred single dose of an agent comprises between about 1 microgram×kilogram$^{-1}$ and about 10 milligram×kilogram$^{-1}$ body weight of an animal. An even more preferred single dose of an agent comprises between about 5 microgram×kilograms' and about 7 milligram×kilogram$^{-1}$ body weight of an animal. An even more preferred single dose of an agent comprises between about 10 microgram×kilograms' and about 5 milligram×kilograms' body weight of an animal. A particularly preferred single dose of an agent comprises between about 0.1 milligram×kilograms and about 5 milligram×kilograms body weight of an animal, if the an agent is delivered by aerosol. Another particularly preferred single dose of an agent comprises between about 0.1 microgram×kilograms$^{-1}$ and about 10 microgram×kilogram$^{-1}$ body weight of an animal, if the agent is delivered parenterally. These doses particularly apply to the administration of protein agents, antibodies, and/or small molecules (i.e., the products of drug design).

In one embodiment, the agent is administered with a pharmaceutically acceptable carrier, which includes pharmaceutically acceptable excipients and/or delivery vehicles, for administering the agent to a patient (e.g., a chimeric antibody or a liposome delivery vehicle). As used herein, a pharmaceutically acceptable carrier refers to any substance suitable for delivering an agent useful in the method of the present invention to a suitable in viivo or ex vivo site. Preferred pharmaceutically acceptable carriers are capable of maintaining an agent of the present invention in a form that, upon arrival of the agent in the animal and/or at a target γδ T cell, the agent is capable of interacting with its target (i.e., the γδ T cell) such that AHR is reduced or prevented. Suitable excipients of the present invention include excipients or formularies that transport or help transport, but do not specifically target an agent to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters, glycols and dry-powder inhalers. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal,—or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into an animal. As used herein, a controlled release formulation comprises an agent of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Suitable delivery vehicles include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of an agent at that site. Suitable modifications include manipulating the chemical formula of the lipid portion of the delivery vehicle and/or introducing into the vehicle a targeting agent (e.g., an antibody) capable of specifically targeting a delivery vehicle to a preferred site (e.g., a γδ T cell). Other suitable delivery vehicles include gold particles, poly-L-lysine/DNA-molecular conjugates, and artificial chromosomes. In one embodiment, when the route of delivery is inhaled, a composition or agent of the present invention can be delivered by an inhaler device.

A pharmaceutically acceptable carrier which is capable of targeting is herein referred to as a "delivery vehicle." Delivery vehicles of the present invention are capable of delivering a formulation, including an agent that increases the action of γδ T cells, to a target site in a mammal. A "target site" refers to a site in a mammal to which one desires to deliver a therapeutic formulation. For example, a target site can be any cell which is targeted by direct injection or delivery using antibodies (e.g., monospecific, chimeric or bispecific antibodies) liposomes, viral vectors or other delivery vehicles, including ribozymes. Examples of delivery vehicles include, but are not limited to, antibodies, artificial and natural lipid-containing delivery vehicles, viral vectors, and ribozymes. Natural lipid-containing delivery vehicles include cells and cellular membranes. Artificial lipid-containing delivery vehicles include liposomes and micelles. A delivery vehicle of the present invention can be modified to target to a particular site in a mammal, thereby targeting and making use of a nucleic acid molecule at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

In one embodiment, an agent of the present invention is targeted to a γδ T cell by using an antibody that selectively binds to a protein expressed on the surface of the target γδ T cell. Preferably, the antibody binds to a γδ T cell receptor, with γδ T cell receptors comprising a Vγ4 chain being particularly preferred. Such an antibody can include functional antibody equivalents such as antibody fragments (e.g., Fab fragments or Fab$_2$ fragments) and genetically-engineered antibodies, including single chain antibodies or chimeric antibodies, including bi-specific antibodies that can bind to mnore than one epitope. Such targeting antibodies are complexed with an agent that increases the action of the γδ T cell that is targeted, and serves to deliver the agent to the γδ T cell. The antibodies can be complexed to the target by any suitable means, including by complexing with a liposome, or by recombinant or chemical linkage of the agent to the antibody. In one embodiment, the agent is a second antibody or portion thereof that stimulates a γδ T cell and that forms a chimeric or bispecific antibody with the targeting antibody.

The method of the present invention can be used in any animal, and particularly, in any animal of the Vertebrate class, Mammalia, including, without limitation, primates, rodents, livestock and domestic pets. Preferred mammals to treat using the method of the present invention include humans.

Yet another embodiment of the present invention relates to a method to identify a compound that reduces or prevents airway hyperresponsiveness by increasing the action of γδ T cells. Such a method includes the steps of: (a) contacting a putative regulatory compound with a γδ T cell; (b) detecting whether the putative regulatory compound increases γδ T cell action; and, (c) administering the putative regulatory compound to a non-human animal in which airway hyperesponsiveness can be induced and identifying animals in which airway hyperresponsiveness is reduced or prevented as compared to in the absence of the putative regulatory compound. Preferably, the γδ T cell is contacted with the regulatory compound under conditions wherein, in the absence of the putative regulatory compound, the action of the γδ T cell is not substantially increased (i.e., is at a resting, or baseline, level). A putative regulatory compound that increases γδ T cell action and that reduces or prevents airway hyperresponsiveness in the non-human animal is indicated to be a compound for reducing or preventing airway hyperresponsiveness.

In this method, the step (b) of detecting can include, but is not limited to, a method selected from the group of measurement of measurement proliferation of said γδ T cell, measurement of cytokine production by said γδ T cell, measurement of calcium mobilization in said γδ T cell, measurement of cytokine receptor expression by said γδ T cell, measurement of CD69 upregulationby said γδ T cell, measurement of upregulation of CD44 by said γδ T cell, and measurement of cytoskeletal reorganization by said γδ T cell. Such methods are known in the art and are described above.

In an alternate embodiment, such a method can include the steps of: (a) contacting a putative regulatory compound with an isolated γδ T cell and determining whether the putative regulatory compound binds to the γδ T cell (e.g., preferably to the γδ T cell receptor); an optional step (b) of further detecting whether compounds that bind to γδ T cell in (a) increase the action of γδ T cells in an assay for γδ T cell biological activity (e.g., a proliferation or cytokine assay); and (c) administering the putative regulatory compound to a non-human animal in which airway hyperresponsiveness can be induced and identifying animals in which airway hyperresponsiveness is reduced or prevented as compared to in the absence of the putative regulatory compound.

Yet another alternate embodiment of the method to identify a compound that reduces or prevents airway hyperresponsiveness associated with inflammation, includes the steps of: (a) contacting a cell or cell lysate which expresses a γδ T cell receptor with a putative regulatory compound; (b) detecting whether the putative regulatory compound stimulates a γδ T cell receptor function selected from the group of γδ T cell receptor expression, γδ T cell ligand binding or γδ T cell receptor biological activity (e.g., stimulation of proliferation, stimulation of cytokine production by a γδ T cell); and (c) administering the putative regulatory compound to a non-human animal in which airway hyperresponsiveness can be induced, and identifying animals in which airway hyperresponsiveness is reduced or prevented as compared to in the absence of the putative regulatory compound. A putative regulatory compound that inhibits γδ T cell receptor expression, ligand binding or biological activity and that reduces or prevents airway hyperresponsiveness in the non-human animal is indicated to be a compound for reducing or preventing hyperresponsiveness associated with inflammation.

In one alternate embodiment, step (a) of contacting comprises contacting the putative regulatory compound with a cell or cell lysate containing a reporter gene operatively associated with a regulatory element of the γδ T cell receptor, and step (b) of detecting comprises detecting increased expression of the reporter gene product. In another aspect of this embodiment, step (a) of contacting comprises contacting the putative regulatory compound with a cell or cell lysate containing transcripts of the γδ T cell receptor, and step (b) of detecting comprises detecting translational activation of the γδ T cell receptor transcript.

As used herein, the term "putative" refers to compounds having an unknown or previously unappreciated regulatory activity in a particular process. As such, the term "identify" is intended to include all compounds, the usefulness of which as a regulatory compound of γδ T cell action for the purposes of reducing airway hyperresponsiveness is determined by a method of the present invention.

The above described methods, in one aspect, involve contacting cells with the compound being tested for a sufficient time to allow for interaction of the putative regulatory compound with the γδ T cell and in one embodiment, with the γδ T cell receptor expressed by the cell. The period of contact with the compound being tested can be varied depending on the result being measured, and can be determined by one of skill in the art. For example, for binding assays, a shorter time of contact with the compound being tested is typically suitable, than then activation is assessed. As used herein, the term "contact period" refers to the time period during which cells are in contact with the compound being tested. The term "incubation period" refers to the entire time during which cells are allowed to grow prior to evaluation, and can be inclusive of the contact period. Thus, the incubation period includes all of the contact period and may include a further time period during which the compound being tested is not present but during which growth or cytokine production is continuing (in the case of a cell based assay) prior to scoring. The incubation time for growth of cells can vary but is sufficient to allow for the binding of the γδ T cell receptor and/or increased action of the γδ T cell. It will be recognized that shorter incubation times are preferable because compounds can be more rapidly screened. A preferred incubation time is between about 1 minute to about 72 hours.

The above-described methods for identifying a compound of the present invention include contacting a γδ T cell or a γδ T cell lysate with a compound being tested for its ability to bind to and/or regulate the action of the γδ T cell or its receptor, respectively. The conditions under which the cell or cell lysate of the present invention is contacted with a putative regulatory compound, such as by mixing, are any suitable culture or assay conditions and includes an effective medium in which the cell can be cultured or in which the cell lysate can be evaluated in the presence and absence of a putative regulatory compound. For example, γδ T cells or other suitable cells expressing a γδ T cell receptor (i.e., the test cells) can be grown in liquid culture medium or grown on solid medium in which the liquid medium or the solid medium contains the compound to be tested. In addition, as described above, the liquid or solid medium contains components necessary for cell growth, such as assimilable carbon, nitrogen and micronutrients. Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. Cells are contacted with a putative regulatory compound under conditions which take into account the number of cells per container contacted, the concentration of putative regulatory compound(s) administered to a cell, the incubation time of the putative regulatory compound with the cell, and the concentration of compound administered to a cell. Determination of effective protocols can be accomplished by those skilled in the art based on variables such as the size of the container, the volume of liquid in the container, conditions known to be suitable for the culture of γδ T cells, and the chemical composition of the putative regulatory compound (i.e., size, charge etc.) being tested. A preferred amount of putative regulatory compound (s) comprises between about 1 nM to about 10 mM of putative regulatory compound(s) per well of a 96-well plate.

Suitable cells for use with the present invention include any γδ T cell and in assays which only require the expression of a γδ T cell receptor, any cell that has been transfected with and expresses a γδ T cell receptor. γδ T cells can include normal γδ T cells (i.e., native, or natural isolates), T cell clones (i.e., a natural isolate that has been clonally selected and expanded), or γδ T cell hybridomas (i.e., natural isolates that have been fused with a myeloma cell line to produce an immortalized T cell hybrid). In one embodiment, host cells genetically engineered to express a functional γδ T cell receptor that responds to activation by known stimulators of γδ T cells can be used as an endpoint in the assay; e.g., as measured by a chemical, physiological, biological, or phenotypic change, induction of a host cell gene or a reporter gene, change in cAMP levels, activity of other intracellular signal transduction molecules, proliferation, differentiation, etc. Cytokine-producing cells for use with the present invention include mammalian, invertebrate, plant, insect, fungal, yeast and bacterial cells. Preferred cells include mammalian, amphibian and yeast cells. Preferred mammalian cells include primate, non-human primate, mouse and rat. In one embodiment, the test cell (host cell) should express a functional γδ T cell receptor that gives a significant response to stimulation through the γδ T cell receptor, preferably greater than 2, 5, or 10-fold induction over background.

As disclosed above, the present methods also make use of non-cell based assay systems to identify compounds that can regulate AHR. For example, isolated membranes may be used to identify compounds that interact with the γδ T cell receptor being tested. Membranes can be harvested from cells expressing γδ T cell receptors by standard techniques and used in an in vitro binding assay. A $^{125}$I-labeled γδ T cell receptor ligand is bound to the membranes and assayed for specific activity; specific binding is determined by comparison with binding assays performed in the presence of excess unlabeled ligand. Membranes are typically incubated with labeled ligand in the presence or absence of test compound. Compounds that bind to the receptor and compete with labeled ligand for binding to the membranes reduced the signal compared to the vehicle controlsamples.

Alternatively, soluble γδ T cell receptors may be recombinantly expressed and utilized in non-cell based assays to identify compounds that bind to γδ T cell receptors. Recombinantly expressed γδ T cell receptor polypeptides or fusion proteins containing one or more extracellular domains of a γδ T cell receptor can be used in the non-cell based screening assays. Alternatively, peptides corresponding to one or more of the cytoplasmic domains of the γδ T cell receptor or fusion proteins containing one or more of the cytoplasmic domains of the γδ T cell receptor can be used in non-cell based assay systems to identify compounds that bind to the cytoplasmic portion of the γδ T cell receptor; such compounds may be useful to modulate the signal transduction pathway of the γδ T cell receptor. In non-cell based assays the recombinantly expressed γδ cell receptor is attached to a solid substrate such as a test tube, microtitre well or a column, by means well known to those in the art. The test compounds are then assayed for their ability to bind to the γδ T cell receptor.

As discussed above, in vitro cell based assays may be designed to screen for compounds that regulate γδ T cell receptor expression at either the transcriptional or translational level. In one embodiment, DNA encoding a reporter molecule can be linked to a regulatory element of a γδ T cell receptor gene and used in appropriate intact cells, cell extracts or lysates to identify compounds that modulate γδ T cell receptor gene expression, respectively. Appropriate cells or cell extracts are prepared from any cell type that normally expresses a γδ T cell receptor gene, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

To identify compounds that regulate γδ T cell receptor translation, cells or in vitro cell lysates containing γδ T cell receptor transcripts may be tested for modulation of γδ T cell receptor mRNA translation. To assay for inhibitors of translation, test compounds are assayed for their ability to modulate the translation of γδ T cell receptor mRNA in in vitro translation extracts. Compounds that increase the level of γδ T cell receptor expression, either at the transcriptional or translational level, may be useful for reduction of AHR.

Finally, a putative regulatory compound of the present invention can be evaluated by administering putative regulatory compounds to a non-human test animal (and eventually, to a human test subject) and detecting whether the putative regulatory compound reduces AHR in the test animal. Animal models of disease are invaluable to provide evidence to support a hypothesis or justify human experiments. For example, mice have many proteins which share greater than 90% homology with corresponding human proteins. Preferred modes of administration, including dose, route and other aspects of the method are as previously described herein for the therapeutic methods of the present invention. The test animal can be any suitable non-human animal, including any test animal described in the art for evaluation of AHR. The test animal can be, for example, an established mouse model of AHR, as previously described (see, for example, Takeda et al., (1997). *J. Exp. Med.* 186, 449-454; Renz et al., 1992, *J. Allergy Clin. Immunol.* 89:1127-1138; Larsen et al., 1992, *J. Clin. Invest.* 89:747-752; and Saloga et al., 1993, *J. Clin. Itivest.* 91:133-141). This non-human model system is an accepted model of airway hyperresponsiveness associated with allergic inflammation which shares many characteristics with human respiratory conditions associated with allergic inflammation, including airway hyperresponsiveness, airway fibrosis, increased IgE production, and eosinophilia. More specifically, the mouse model is an antigen-driven minrine system that is characterized by an immune (IgE) response, a dependence on a Th2-type response, and an eosinophil response, and is a valid model for studying allergic inflammation of the airways in mammals, and particularly in humans. The model is characterized by both a marked and evolving hyperresponsiveness of the airways. Briefly, as an exemplary protocol for this murine model, mice (typically BALB/c) are immunized intraperitoneally with ovalbumin (OVA). The mice are then chronically exposed (i.e., challenged) for 8 days (i.e., 8 exposures of 30 minutes each in 8 days) to aerosolized OVA. It should be noted that both immunization and subsequent antigen challenge are required to observe a response in mice. To characterize the murine model, pulmonary function measurements of airway resistance ($R_L$) and dynamic compliance ($C_L$) and hyperresponsiveness are obtained as described in Example 1 below.

Compounds identified by any of the above-described methods can be used in a method for the reduction or prevention of AHR as described herein.

The following examples are provided for the purposes of illustration and are not intended to limit the scope of the present invention.

EXAMPLES

Example 1

The following example demonstrates that airway reactivity is increased in the absence of γδ T cells.

The following materials and methods are used throughout the examples herein, as indicated.

Animals. The influence of γδ and αβ cells on airway hyperresponsiveness (AHR) was assessed in a murine model of allergen-induced, T cell-dependent asthma. For these experiments, BALB/c mice, C57BL/6 mice, TCR-$\beta^{-/-}$ mice (mice deficient in αβ T cells and back-crossed onto C57BL/6 genetic background), and TCR-$\delta^{-/-}$ mice (mice deficient in γδ T cells and back-crossed onto C57BL/6 genetic background) were purchased from The Jackson Laboratory (Bar Harbor, Me.), and cared for at National Jewish Medical and Research Center (Denver, Colo.) following guidelines for immunodeficient animals.

Sensitization and airway challenge. Mice (BALB/c, C57BL/6, TCR-$\beta^{-/-}$ and TCR-$\delta^{-/-}$) were treated with hamster Ig (sham depletion) or with monoclonal antibody against TCR-δ or TCR-β and received one of the following treatments: (1) no ovalbumin (OVA) treatment (denoted "NT"); (2) airway exposure to nebulized OVA (1% in saline) alone, using ultrasonic nebulization (particle-size 3-5 $\mu m^2$) for 20 minutes on three consecutive days (denoted "3N"); or (3) sensitization to OVA by intraperitoneal injection of 20 μg of OVA (Grade V; Sigma) emulsified in 2.25 mg alum (Alumimuject®; Pierce, Rockford, Ill.) in a total volume of 100 μl on days 0 and 14, followed by aerosolized airway challenge with nebulized OVA on days 28, 29 and 30 (denoted "2ip3N"). Determination of airway responsiveness and inflammation was assessed 48 hours after the last nebulized OVA exposure for 3N- and 2ip3N-treated mice. For each of these treatments and type of mice, groups of four mice were analyzed in each independent experiment.

Determination of airway responsiveness. Airway responsiveness was assessed as a change in airway function after challenge with aerosolized methacholine (MCh) through the airways. Anesthetized and tracheostomized mice were mechanically ventilated, and lung function was assessed as a modification to known procedures. Briefly, a four-way connector was attached to the tracheotomy tube (stainless steel cannula, 18-gauge, with two ports connected to the inspiratory and expiratory sides of two ventilators). Ventilation was achieved at 160 breaths per minute and a tidal volume of 0.15 ml with a positive end-expiratory pressure of 2-4 cm $H_2O$ (model 683; Harvard apparatus, South Natwick, Mass.). Aerosolized MCh was administered for 10 breaths at rate of 60 breaths/min in increasing concentrations (1.56, 3.125, 6.25 and 12.5 mg/ml MCh for BALB/c mice, 6.25, 12.5, 25, 50 and 100 mg/ml MCh for C57BL/6 mice) with a tidal volume of 0.5 ml by the second ventilator (model SN-480-7-3-2T; Shineno Manufacturing, Tokyo, Japan). The chamber containing the mouse was continuous with a 1.0-liter glass bottle filled with copper gauze to stabilize the volume signal for thermal drift. Transpulmonary pressure was detected by a pressure transducer with one side connected to the fourth port of a four-way connector and the other side connected to a second port on the plethysmograph. Changes in lung volume were measured by detecting pressure changes in the plethysmographic chamber through a port in the connecting tube with a pressure transducer and then referenced to a second copper-gauze filled 1.0-liter glass bottle. Flow was measured by digital differentiation of the volume signal. Lung resistance ($R_L$) and dynamic compliance (C) were continuously computed (Labview; National Instruments, Austin, Tex.) by fitting flow, volume and pressure to an equation of motion. After each aerosol MCh challenge, the data were continuously collected for 1-5 min. and maximum values of $R_L$, and minimum values of C were used to express changes in murine airway function.

Depletion with monoclonal antibody against TCR. Depletion was achieved by injection into the tall vein of 200 μg hamster monoclonal antibodies against TCR-δ (mixture of GL3 (PharMingen) and 403.A10) or TCR-β (H57-597 (PharMingen)). Sham depletion was accomplished with hamster Ig (Jackson Laboratories, Bar harbor, Me.).

Broncho alveolar lavage (BAL) fluid. Immediately after assessment of AHR, lungs were lavaged through the tracheal tube with Hank's balanced solution (HB55 1×1 ml using 1 lavage injection with 1 ml of HBSS at 37° C.). The volume of and number of cells in the BAL fluid were assessed (Coulter Counter; Coulter, Hialeah, Fla.). BAL fluid cells were stained with Leukostate (Fischer Diagnostics, Pittsburgh, Pa.) on cytosine slides and differentiated by experimenters "blinded" to sample identity counting at least 200 cells with a light microscope.

Histologic examination. Lungs were inflated through the tracheas and fixed with 10% formaldehyde. The left lung was excised and embedded in paraffin, and tissue sections 5 μm in thickness were affixed to slides and deparaffinized. Sections were stained with hematoxlin and eosin and the inflammatory reaction assessed by light microscopy.

Eosinophils and major basic protein staining. A FITC-conjugated rabbit monoclonal antibody against mouse major basic protein was used to assess eosinophil numbers by immunohistochemistry. Positive events were counted in the submucosatissue around central airways using the IPLab2 software (Signal Analytics, Vienna, Va.) counting four different sections per animal.

Statistical analysis. All results are expressed as the mean and standard deviation (s.d.) except where otherwise indicated. Analysis of variance was used to determine the levels of difference between all groups. Pairs of groups were compared by unpaired two-tailed Student's t-test. P values were considered significant at 0.05.

Results. As previously shown by studies that established the role of αβ T cells in the development of AHR (Hamelmann et al., 1996, *J. Exp. Med.* 183:1719-1729; Takeda et al., 1997, *J. Exp. Med.* 186:449-454), C57BL/6 mice that were systemically sensitized to ovalbumin (OVA) and challenged through the airways developed AHR to inhaled methacholine (MCh), whereas untreated mice or those exposed to OVA only through the airways did not (FIG. 1A). FIG. 1A shows the $R_L$ changes in normal C57BL/6 mice after 2ip3N treatment (■), 3N treatment (□) and untreated (◇). There were no differences in baseline responses to saline in any of these groups. R baseline values (in cm $H_2O$/ml per second) were 0.56±0.04 (2ip3N), 0.57±0.03 (3N) and 0.53±0.03 (NT) P(0.05, 2ip3N compared with 3N).

Figure 1B:
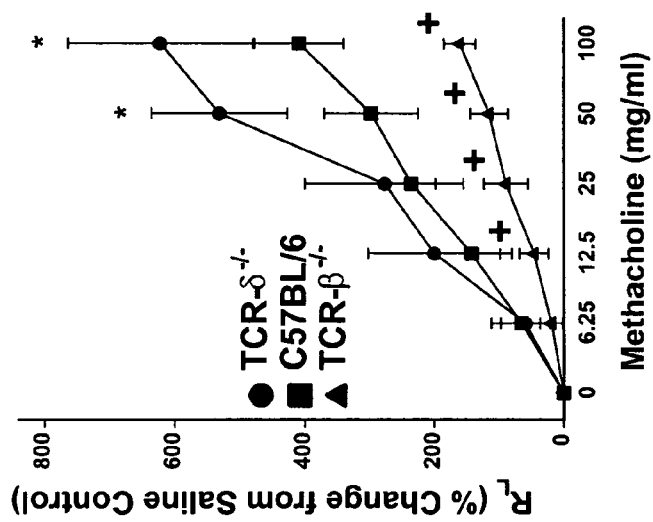
FIG. 1B is a line graph showing changes in airway resistance ($R_L$) in TCR-$\delta^{-/-}$ mice, TCR-$\beta^{-/-}$ mice and normal C57BL/6 after systemic airway sensitization.
Figure 1A:
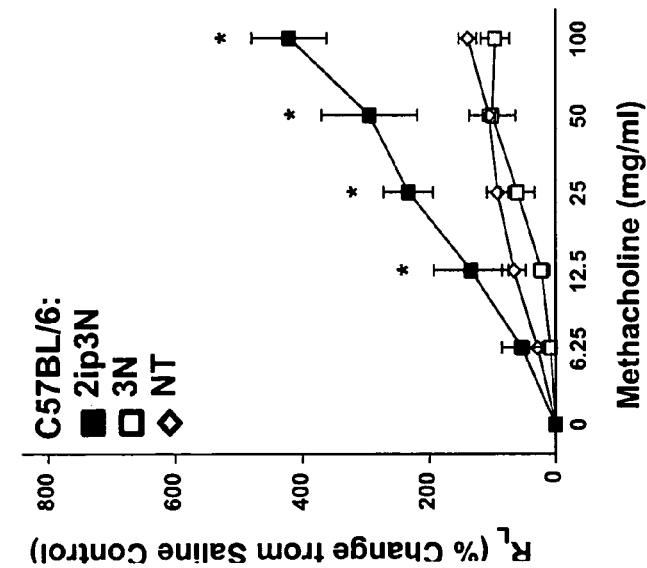
FIG. 1A is a line graph showing changes in airway resistance ($R_L$) in normal C57BL/6 mice after systemic airway sensitization, aerosol only airway sensitization, and no treatment.

Mice genetically deficient to γδ T cells (T-cell receptor (TCR)-$δ^{-/-}$) also developed AHR, in contrast to mice deficient in αβ T cells (TCR-$β^{-/-}$) (FIG. 1B). FIG. 1B shows $R_L$ changes in TCR-$δ^{-/-}$ (●), TCR-$β^{-/-}$ (▲) and normal C57BL/6 (■) mice after 2ip3N treatment inset. There were no significant differences indicated in baseline responses to saline (data not shown). However, in contrast to a report emphasizing the enhancement of allergic airway inflammation by γδ T cells on AHR (Zuany-Amorim et al., 1998, *Science* 280:1265-1267), the present inventors detected increased responsiveness to MCh in the absence of γδ T cells, indicating a suppressive effect of γδ T cells on AHR in this model. Since both TCR-$β^{-/-}$ And TCR-$δ^{-/-}$ mice had baseline values in airway responsiveness similar to those of the genetically normal control mice (data not shown), background airway tone variations could be ruled out as an explanation of these differences.

Figure 1D:
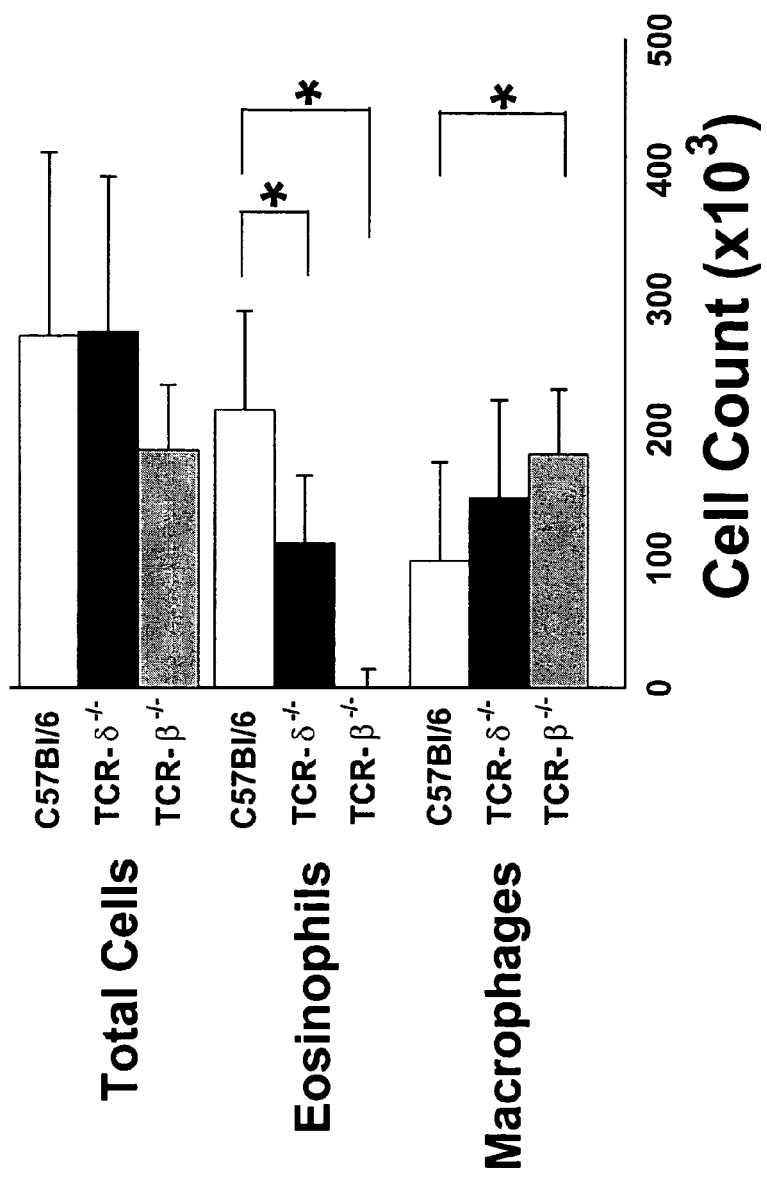
FIG. 1D is a bar graph showing BAL fluid cell composition for total cells, eosinophils and macrophages in C57BL/6 mice, TCR-$\delta^{-/-}$ mice and TCR-$\beta^{-/-}$ mice after systemic airway sensitization.

The broncho alveolar lavage (BAL) fluid and lung sections of C57BL/6 and TCR-$β^{-/-}$ mice challenged systemically and through the airways had similar inflammatory infiltrates with increased eosinophil numbers, whereas TCR-$β^{-/-}$ mice lacked such inflammatory infiltrates (FIG. 1D). FIG. 1D shows the BAL fluid cell composition for total cells, eosinophil and macrophages in 2ip3N-treated C57BL/6, TCR-$δ^{-/-}$ and TCR-$β^{-/-}$ mice. Each bar represents data from at least three independent experiments using 9-12 mice (P<0.05; brackets indicate cell counts being compared; histology not shown). Consistent with previous findings, TCR-$β^{-/-}$ mice had lower numbers of eosinophils in the BAL fluid as well as fewer eosinophils in lung tissue sections, indicating that γδ T cells also influence the influx of eosinophils to the inflammatory sites.

To exclude the possibility of developmental compensatory mechanisms in the genetically TCR-deficient mice, γδ T cells were also depleted in TCR-sufficient mice (i.e., wild type mice) by injecting these mice with monoclonal antibodies against TCR-δ. The results were similar to those in TCR-$δ^{-\backslash -}$ mice, in that AHR was increased in mice depleted of γδ T cells. Moreover, no differences after treatment with monoclonal antibodies against TCR-δ were found in the responses between C57BL/6 and BALB/c mice, two strains known to differ in their airway responsiveness after OVA sensitization and challenge (FIG. 1C). FIG. 1C shows $R_L$ changes in TCR-δ-depleted (▼) or sham-depleted (▽) BALB/c mice after 2ip3N treatment. There were no significant differences in baseline responses to saline in any of these groups. $R_L$ baseline values (in cm $H_2O$/ml per second) were 0.60±0.03 (sham-depleted) and 0.59±0.02 (TCR-δ-depleted). Each curve represents data from at least three independent experiments using 9-12 mice (P<0.05). Thus, the regulatory effects of γδ T cells in OVA-induced AHR seem to be independent of these genetic differences. The cellular composition in BAL fluid and lung tissue of the antibody-depleted mice was also similar to that found in the genetically deficient mice (data not shown).

Based on these findings, it was concluded that, during allergic αβ T cell-dependent AHR, γδ T-cell deficiency results in increased airway responsiveness, despite a concurrent reduction in eosinophilic inflammation.

Example 2

The following example demonstrates that the effect of γδ T cells on airway hyperresponsiveness does not require systemic sensitization.

Since γδ T-cell deficiency was shown to influence AHR in allergen-sensitized and challenged mice (Example 1), it was next determined whether systemic sensitization with antigen was necessary for these effects to be shown. In this experiment, the effect γδ T cells on mice sensitize only through the airways was investigated, using the protocol described above (3N treatment).

Figures 2A, 2B, 2C:
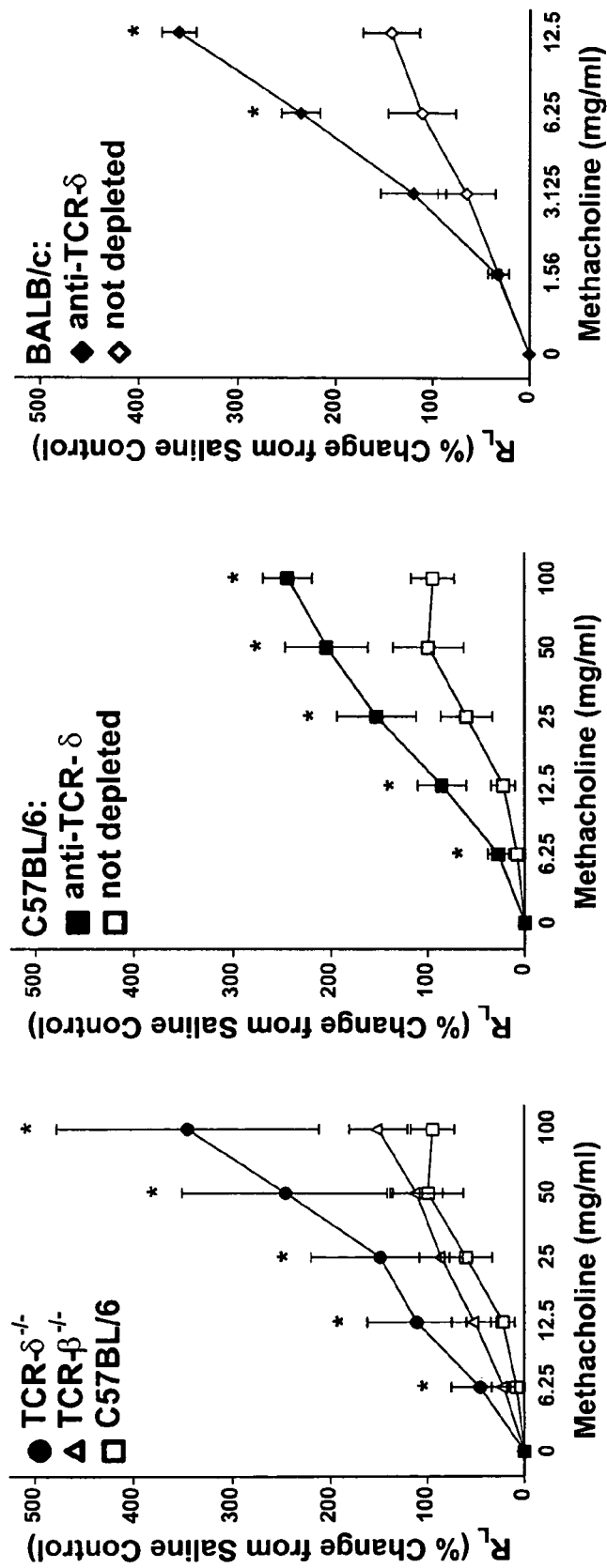
FIG. 2A is a line graph showing changes in airway resistance ($R_L$) in C57BL/6 mice, TCR-$\delta^{-/-}$ mice and TCR-$\beta^{-/-}$ mice after aerosol only airway sensitization.
FIG. 2B is a line graph showing changes in dynamic compliance ($C_{dyn}$) in C57BL/6 mice, TCR-$\delta^{-/-}$ mice and TCR-$\beta^{-/-}$ mice after aerosol only airway sensitization.
FIG. 2C is a line graph showing changes in airway resistance ($R_L$) in sham-depleted C57BL/6 mice and γδ T cell-depleted C57BL/6 mice after aerosol only airway sensitization.
Figures 2D, 2E, 2F:
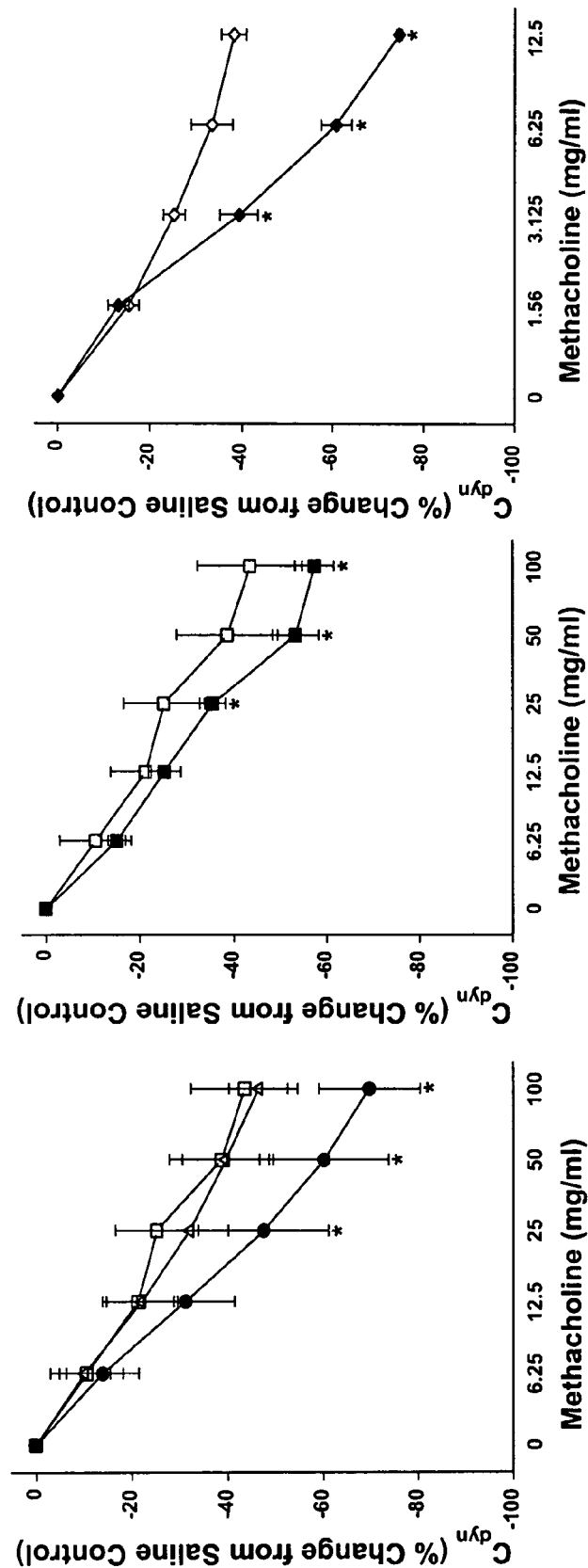
FIG. 2D is a line graph showing changes in dynamic compliance ($C_{dyn}$) in sham-depleted C57BL/6 mice and γδ T cell-depleted C57BL/6 mice after aerosol only airway sensitization.
FIG. 2E is a line graph showing changes in airway resistance (RL) sham-depleted BALB/c mice and γδ T cell-depleted BALB/c mice after aerosol only airway sensitization.
FIG. 2F is a line graph showing changes in dynamic compliance ($C_{dyn}$) sham-depleted BALB/c mice and γδ T cell-depleted BALB/c mice after aerosol only airway sensitization.
Figure 2G:
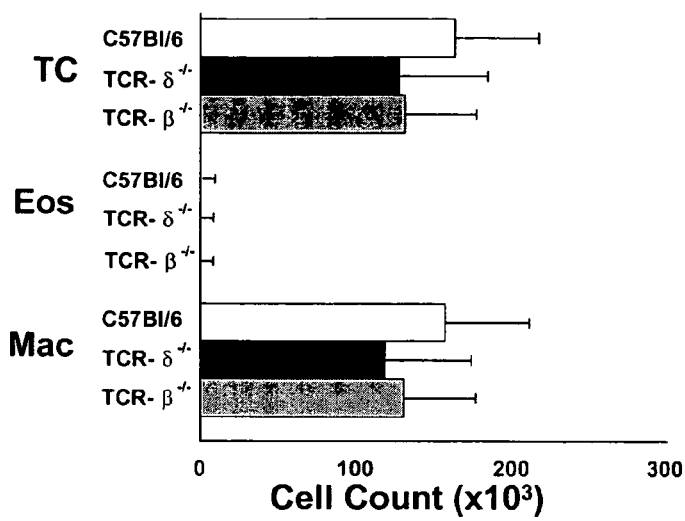
FIG. 2G is a bar graph showing BAL fluid cell composition for total cells, eosinophils and macrophages in C57BL/6 mice, TCR-$\delta^{-/-}$ mice and TCR-$\beta^{-/-}$ mice after aerosol only airway sensitization.

Results are shown in FIGS. 2A-2I. FIGS. 2A, 2C and 2G illustrate changes in airway resistance ($R_L$); FIGS. 2B, 2D and 2F illustrate changes in dynamic compliance (C). FIGS. 2A and 2B show the effects of 3N treatment in C57BL/6 (□), TCR-$δ^{-/-}$ (●) and TCR-$β^{-/-}$ (▲) mice. FIGS. 2C and 2D show the effects of 3N treatment in sham-depleted (□) and γδ T cell-depleted (■) C57BL/6 mice. FIGS. 2E and 2F show the effects of 3N treatment in sham-depleted (◇) and γδ T cell-depleted (◆) BALB/c mice. There were no significant differences in responses to saline in any of these groups. RL baseline values in cm-$H_2O$/ml per second) were 0.59±0.08 (TCR-$δ^{-/-}$); 0.57±0.03 (C57BL/6); 0.59±0.07 (TCR$^{-/-}$); 0.57±0.03 (sham-depleted C57BL/6); 0.62±0.08 (TCR-δ-depleted C57BL/6); 0.54±0.04 (sham-depleted BALB/c); 0.56±0.04 (TCR-δ-depleted BALB/c). Each curve represents data from at least three independent experiments using 9-12 mice (P<0.05).

Figure 2H:
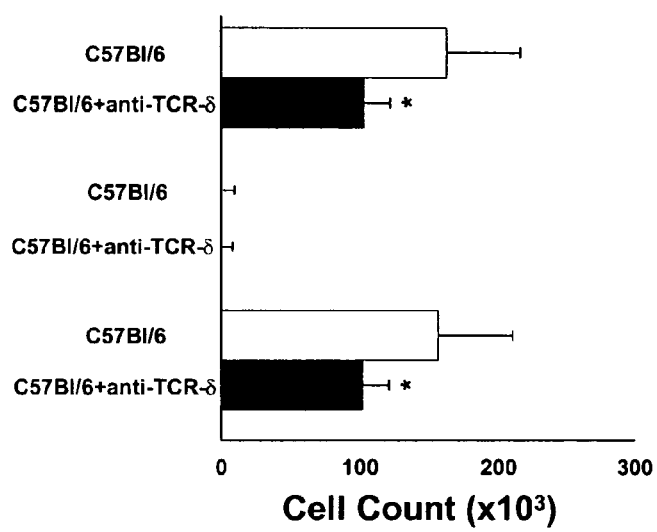
FIG. 2H is a bar graph showing BAL fluid cell composition for total cells, eosinophils and macrophages in sham-depleted C57BL/6 mice and γδ T cell-depleted C57BL/6 mice after aerosol only airway sensitization.
Figure 2I:
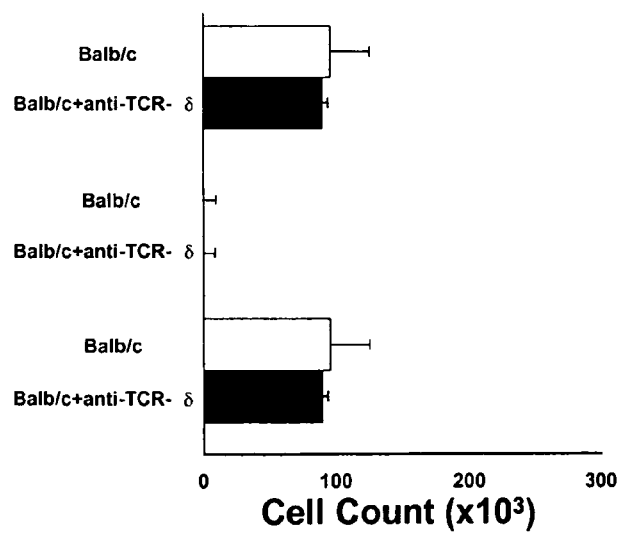
FIG. 2I is a bar graph showing BAL fluid cell composition for total cells, eosinophils and macrophages in sham-depleted BALB/c mice and γδ T cell-depleted BALB/c mice after aerosol only airway sensitization.

FIG. 2G shows the BAL fluid cell composition for total cells (TC), eosinophil (EOS) and macrophages (Mac) in 3N-tested mice; C57BL/6, TCR-$δ^{-/-}$, TCR-$β^{-/-}$ mice. FIG. 2H shows the BAL fluid cell composition of these cells in sham-depleted and γδ T cell-depleted C57BL/6 mice. FIG. 2I shows the BAL fluid cell composition for these cells in BALB/c mice. Each bar represents data from at least three independent experiments using 9-12 mice (P<0.05). The results in FIGS. 2A-2I demonstrated that TCR-$δ^{-/-}$ mice had a higher level of to airway responsiveness than C57BL/6 mice, even when they were exposed to OVA only through the airways (nebulized OVA on 3 consecutive days; 3N treatment). The higher increases in airway responsiveness in TCR-$δ^{-/-}$ mice involved both the larger airways as assessed by airway resistance ($R_L$) (FIG. 2A) and the smaller airways, as demonstrated by changes in dynamic lung compliance (FIG. 2B). As expected, no AER was detectable in TCR-$β^{-/-}$ mice. In mice treated with antibodies to deplete γδ T cells changes in airway function again resembled those of the genetically deficient mice (FIGS. 2C-F). However, despite these obvious changes in airway function, mice deficient in γδ T cells did not demonstrate increases when compared to TCR-sufficient control in inflammatory infiltrates in the BAL fluid or the lung tissue (FIGS. 2G-2I; histology not shown). Thus, in the absence of systemic antigen sensitization and the associated inflammatory response, γδ T cell deficiency was still associated with increased airway responsiveness, indicating a mechanism independent of antigen-specific reactivity, and thus perhaps of αβ T-cell responses.

Example 3

The following example demonstrates that γδ T-cell regulation of AHR is independent of αβ T cells.

Figure 3A:
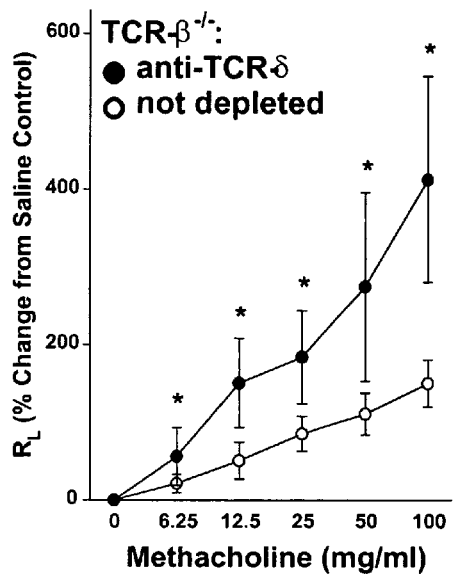
FIG. 3A is a line graph showing changes in airway resistance (RL) in sham-depleted TCR-$\beta^{b-/-}$ mice and γδ-depleted TCR-$\beta^{-/-}$ mice after aerosol only airway sensitization.

To further elucidate the mechanism of the observed increase in AHR corresponding to γδ deficiency, the effect of γδ T-cell depletion on airway responsiveness in 3N-treated mice (see Example 1) was assessed in mice genetically deficient in αβ T cells, by injecting TCR-$\beta^{-/-}$ mice with antibodies against TCR-δ as described in Example 1, followed by evaluation of AHR as described in Example 1. The results of this experiment are shown in FIGS. 3A and 3B (sham-depleted (○) and γδ T cell-depleted (⊙) CR-$\beta^{-/-}$ mice).

Figure 3C:
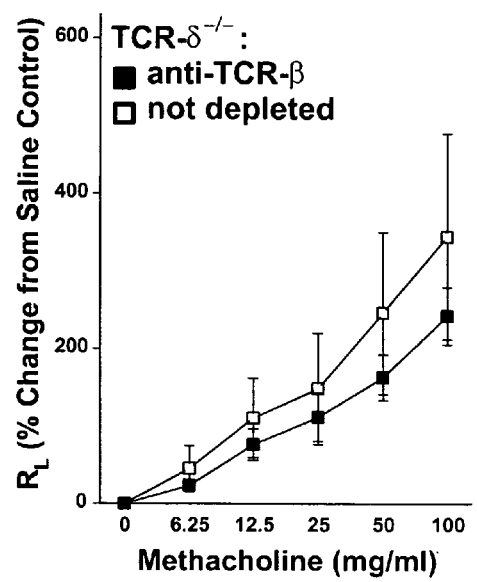
FIG. 3C is a line graph showing changes in airway resistance ($R_L$) in sham-depleted TCR-$\beta^{-/-}$ mice and αβ-depleted TCR-$\beta^{-/-}$ mice after aerosol only airway sensitization.
Figure 3B:
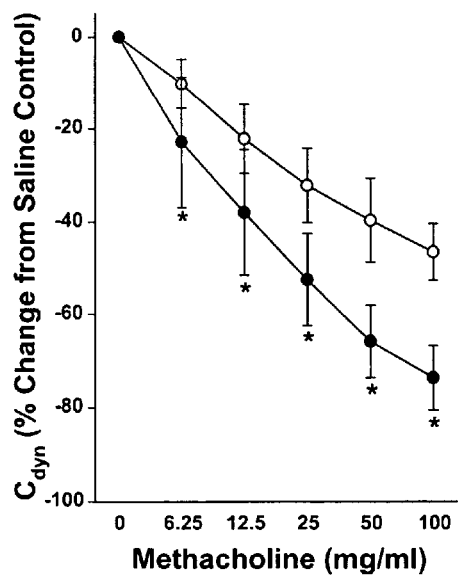
FIG. 3B is a line graph showing changes in dynamic compliance ($C_{dyn}$) in sham-depleted TCR-$\beta^{-/-}$ mice and γδ-depleted TCR-$\beta^{-/-}$ mice after aerosol only airway sensitization.
Figure 3D:
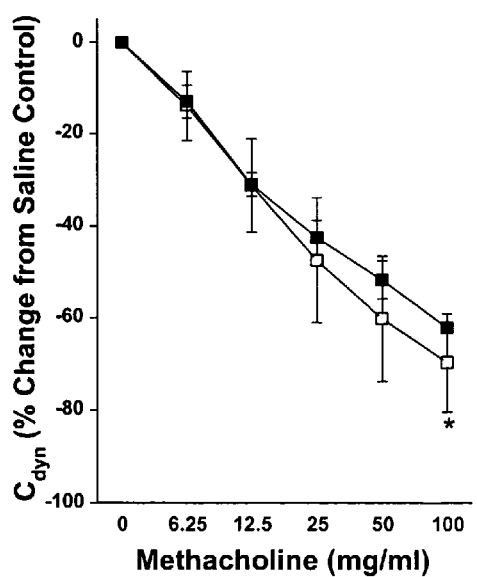
FIG. 3D is a line graph showing changes in dynamic compliance ($C_{dyn}$) in sham-depleted TCR-$\beta^{-/-}$ mice and αβ-depleted TCR-$\beta^{-/-}$ mice after aerosol only airway sensitization.

The reciprocal condition of αβ T-cell depletion in mice genetically deficient in γδ T cells was also assessed using an antibody against TCR-β in TCR-$\delta^{-/-}$ mice, results shown in FIGS. 3C and 3D (sham-depleted (□) and αβ T cell-depleted (■) TCR-$\delta^{-/-}$ mice). As a further control, T cell-deficient mice were treated with antibodies specific for the type of T cells they were lacking (non-relevant treatments). Changes in airway resistance ($R_L$) are shown in FIGS. 3A and 3C; changes in dynamic compliance ($C_{dyn}$) are shown in FIGS. 3B and 3D. There were no significant differences in baseline responses to saline in any of these groups in FIGS. 3A-3D). $R_L$ baseline values (in cm H$_2$O/ml per second) were 0.59±0.08 (sham-depleted TCR-$\beta^{-/-}$); 0.58±0.03 (TCR.δ-depleted TCR-$\beta^{-/-}$); 0.59±0.07 (sham-depleted TCR-$\delta^{-/-}$); 0.57±0.02 (TCR-3-depleted TCR-$\delta^{-/-}$). Sham-depleted mice did not react to nebulized saline exposure alone (open triangles, FIGS. 3A and 3B; open diamonds, FIGS. 3C and 3D). Each curve represents data from at least three independent experiments using 9-12 mice ($P<0.05$).

FIGS. 3E and 3F illustrate BAL fluid cell composition for total cells (TC) eosinophil (EOS) and macrophages (Mac) in 3N-treated mice; sham-depleted and γδ T cell-depleted TCR-$\beta^{-/-}$ mice (FIG. 3E); and in sham-depleted and αβ T cell-depleted TCR-$\delta^{-/-}$ mice (FIG. 3F). Each bar represents data from at least three independent experiments using 9-12 mice.

FIGS. 3A-3D demonstrate that only the depletion of γδ T cells in TCR-$\beta^{-/-}$ mice resulted in increases in AHR. Depletion of αβ T cells in TCR-$\delta^{-/-}$ mice caused a small decrease in AHR. The non-relevant treatments did not produce substantial effects (not shown). Again, BAL fluid (FIGS. 3E and 3F) and lung tissue (not shown) had no inflammatory infiltrates with eosinophil in any of these mice.

Example 4

The following example demonstrates that γδ T-cell regulation is independent of B-cell and cytokine responses.

Since ovalbumin (OVA)-specific immunoglobulin (Ig) production or T-helper 2 (Th2) associated cytokines have been implicated in the development of AHR, serum OVA-specific immunoglobulin production (including IgG$_1$, IgG$_{2a}$, and IgE) as well as interleukin (IL)-4, IL-5 and gamma interferon (IFN γ) levels were measured in the BAL fluid of C57BL/6, TCR-$\beta^{-/-}$ and TCR-$\delta^{-/-}$ mice after 3N (See Example 1: airway exposure to nebulized OVA alone) or 2ip3N treatment (See Example 1: systemic sensitization to OVA).

Figure 4A:
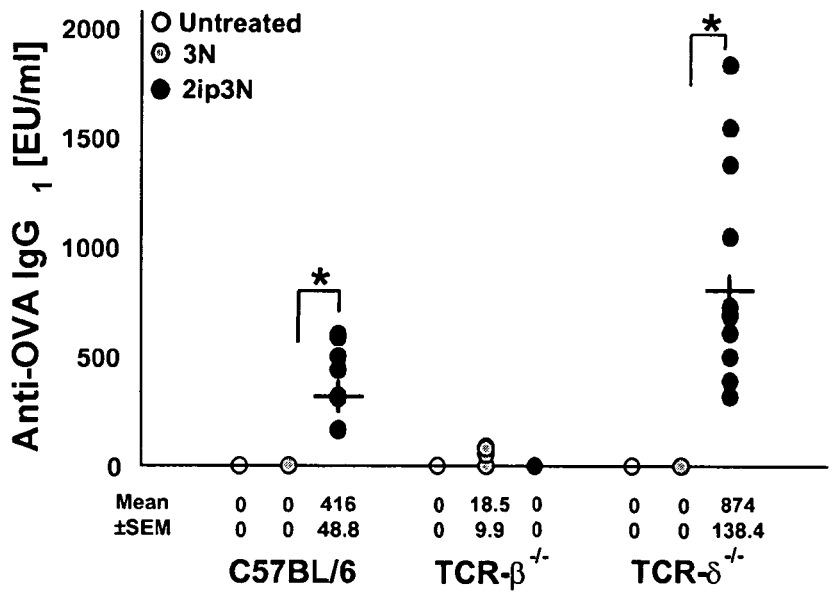
FIG. 4A is a graph showing serum levels of OVA-specific $IgG_1$ in C57BL/6 mice, TCRβ$_{-/-}$ mice, and TCR-δ$_{-/-}$ mice after aerosol only and systemic airway sensitization.
Figure 4B:
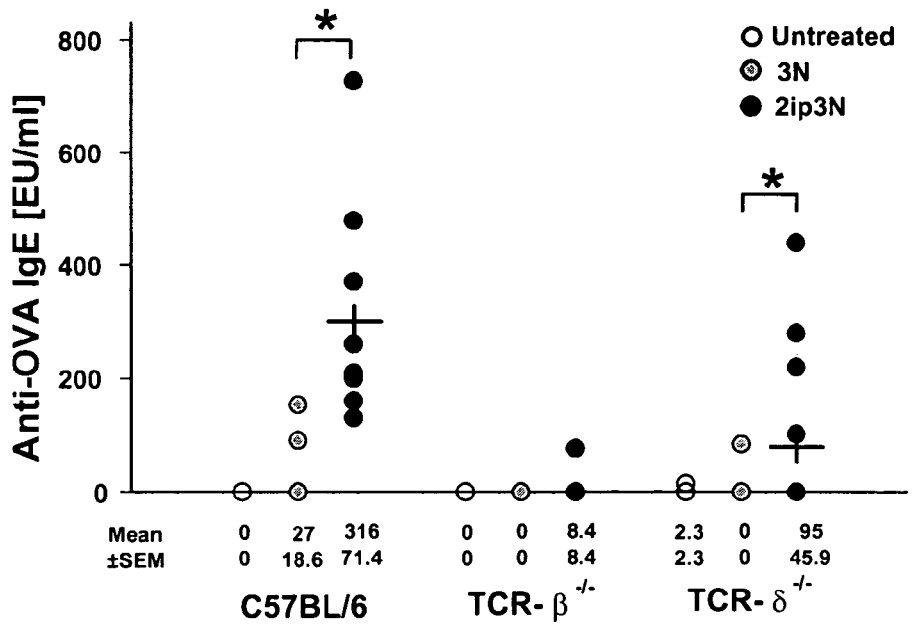
FIG. 4B is a graph showing serum levels of OVA-specific IgE n C57BL/6 mice, TCR-β$_{-/-}$ mice, and TCR-δ$_{-/-}$ mice after aerosol only and systemic airway sensitization.
Figure 4C:
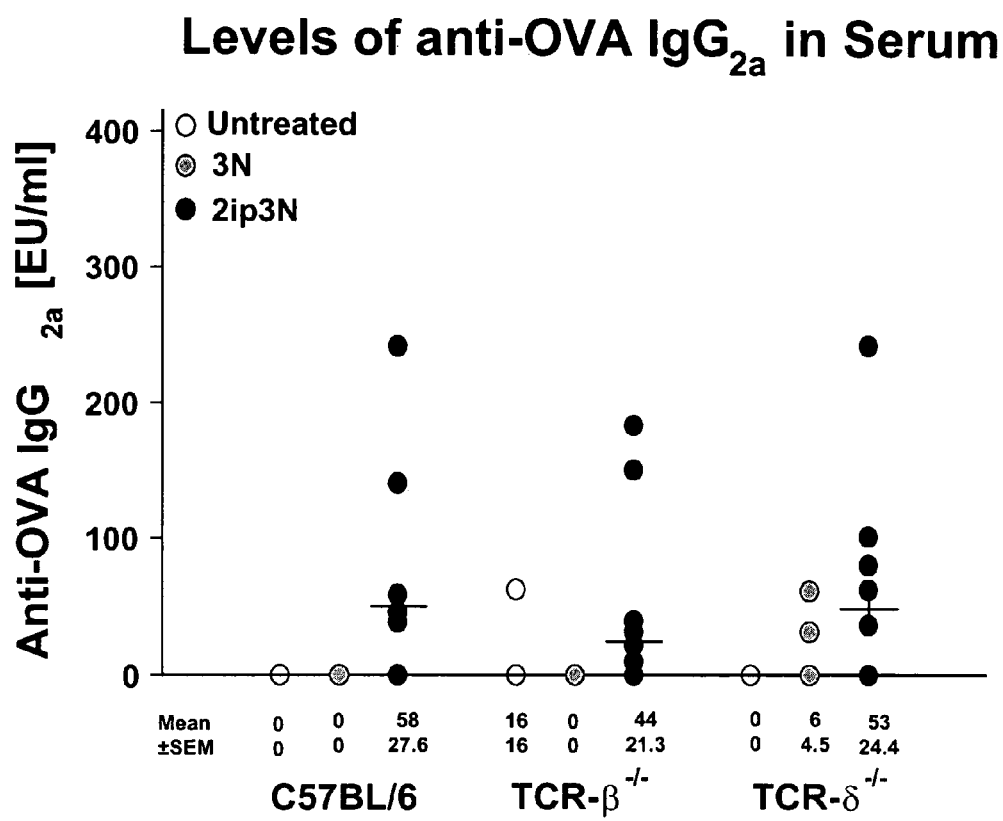
FIG. 4C is a graph showing serum levels of OVA-specific $IgG_{2a}$ in C57BL/6 mice, TCR-β$_{-/-}$ mice, and TCR-δ$_{-/-}$ mice after aerosol only and systemic airway sensitization.

Measurement of antibody against OVA. Serum levels of OVA-specific IgG$_1$, IgG$_{2a}$, and IgE were measured by ELISA. Briefly, serum samples were added to Immulon 2 plates (Dynatech, Chantilly, Va.) coated with 5 μg/ml OVA. OVA-specific IgE was detected with biotinylated antibody against IgE (PharMingen, San Diego, Calif.) and amplified by an avidiniorseradish-peroxidase (Sigma). OVA-specific IgG$_1$ and IgG$_{2a}$ were detected with alkaline phosphatase labeled antibodies (PharMingen, San Diego, Calif.). OVA-specific antibody titers of samples were related to an internal "pooled" standard arbitrarily assigned to be 100 ELISA units (EU). FIGS. 4A-4C show individual levels of OVA-specific IgG$_1$, (FIG. 4A), IgE (FIG. 4B) and IgG$_{2a}$ (FIG. 4C), as defined by ELISA units to an OVA standard, for mice (horizontal axis, mouse strain, n=7-12) left untreated (○) or given 3N(●) or 2ip3N (■) treatment. Crosses represent the means of the immunoglobulin levels (horizontal axis, mean±s.e.m.; $P<0.05$) between levels of immunoglobulin of 3N and 2ip3N-treated mice.

As shown in FIGS. 4A-4C, after 3N treatment, no significant OVA-specific Ig levels were detected in any of the mice, including TCR-$\delta^{-/-}$ mice, despite the fact that the TCR-$\delta^{-/-}$ mice showed increased airway responsiveness after this treatment. As expected, after 2ip3N treatment, αβ T cell-sufficient mice showed increased levels of OVA-specific Ig production whereas αβ T cell-deficient mice did not. OVA-specific IgG may be an exception to this observation, because some of the TCR-$\beta^{-/-}$ mice showed increased levels after 2ip3N treatment (FIG. 4C).

Figure 5A:
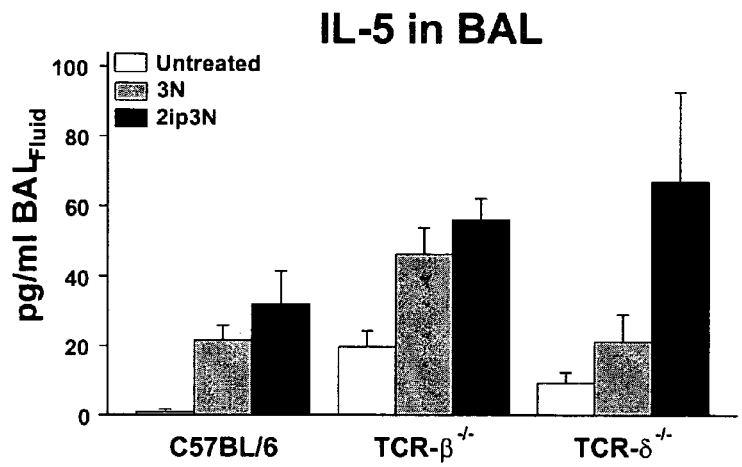
FIG. 5A is a bar graph showing BAL fluid IL-5 levels in C57BL/6 mice, TCR-β$_{-/-}$ mice, and TCR-δ$_{-/-}$ mice after aerosol only and systemic airway sensitization.
Figure 5B:
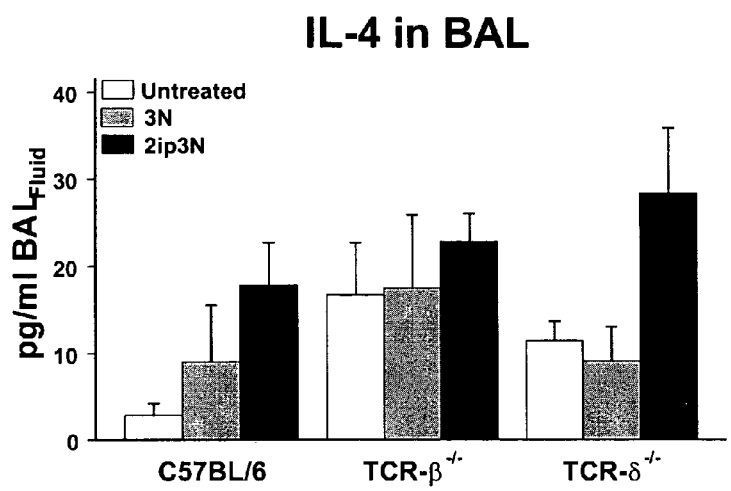
FIG. 5B is a bar graph showing BAL fluid IL-4 levels in C57BL/6 mice, TCR-β$_{-/-}$ mice, and TCR-δ$_{-/-}$ mice after aerosol only and systemic airway sensitization.
Figure 5C:
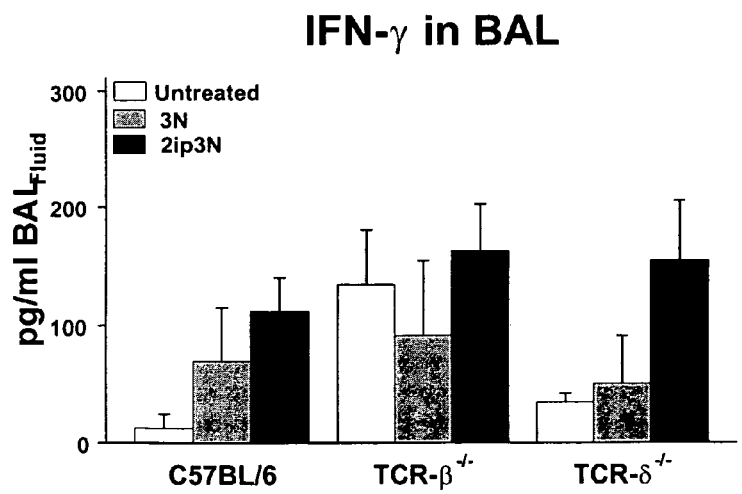
FIG. 5C is a bar graph showing BAL fluid IFN-γ levels in C57BL/6 mice, TCR-β$_{-/-}$ mice, and TCR-δ$_{-/-}$ mice after aerosol only and systemic airway sensitization.

Cytokine levels in BAL fluid. The levels of IFN-γ, IL-4 and IL-5 in BAL fluid were assessed by ELISA. Briefly, samples were added to Immulon 2 plates (Dynatech, Chantilly, Va.) coated with monoclonal antibodies against IFN-γ (clone R4-6A2), IL-4 (clone 11B11) or IL-5 (clone TRFK-5) (all from PharMingen, San Diego, Calif.). Biotinylated monoclonal antibodies against IFN-γ (clone XMG 1.2), IL-4 (clone BVD6-24G2) or IL-5 (clone TRFK-4) (all from PharMingen, San Diego, Calif.) were used for amplified detection. Cytokine levels were calculated by comparison with known cytokine standards with a detection limit of 4 pg/ml for each cytokine. FIGS. 5A-5C show the concentration (pg/ml) of IL-5 (FIG. 5A), IL-4 (FIG. 5B) and IFN-γ (FIG. 5C) in BAL fluid of mice (horizontal axis, strains; n=7-12 mice per treatment) after receiving no treatment (□), 3N (■) treatment, or 2ip3N (■) treatment (error bars: s.e.m.). There were no statistical differences between 3N-treated and 2ip3N-treated mice.

None of the cytokines assessed in the BAL fluid were increased in TCR-$\delta^{-/-}$ mice after 3N treatment (FIGS. 5A-5C), despite increased airway responsiveness after this treatment. The same cytokines were increased after 2ip3N treatment in the αβ T cell-sufficient mice, but not in TCR-$\beta^{-/-}$ mice. However, TCR-$\beta^{-/-}$ mice had increased baseline levels for all of the tested cytokines, despite their lack of airway responsiveness after either 3N or 2ip3N treatments.

The results described here demonstrate a previously unknown γδ T cell-dependent mechanism in the regulation of airway responsiveness, which is independent of αβ T cells and their allergen-specific responses. This experiment shows no evidence to indicate that antibodies are involved in this regulatory mechanism. Furthermore, the increased airway responsiveness in TCR-$\delta^{-/-}$ mice was not correlated with increases in cytokine levels previously suggested to be involved in models allergic inflammation (McMenamin et al., 1994, *Science* 265:186-1871; Zuany-Amorim et al., 1998, supra). These results differ from earlier reports, which have emphasized the role of γδ T cells in regulating allergic αβ T-cell and allergen specific B-cell responses, or their role in promoting allergen-induced eosinophilia and IgE responses (McMenamin et al., 1994, supra; Zuany-Amorim et al., 1998, supra; Schramm et al., 1999, International Conference of the American Thoracic Society; vol. 159:A255 (American Journal of Respiratory and Critical Care Medicine, San Diego, Calif.)). The mechanism of γδ T cell-dependent regulation of airway responses described herein is therefore not restricted to allergic inflammation.

Example 5

The following example demonstrates that, in addition to being independent of αβ T cells, the γδ T cell-dependent regulatory effects on airway responsiveness described herein are not connected to γδ T cell-dependent eosinophilia, further emphasizing the differences from previously reported γδ T cell-dependent mechanisms.

In addition to the independence of αβ T cells, the γδ T cell-dependent regulatory effects on airway responsiveness described herein are in contrast to γδ T cell-dependent eosinophilia, further emphasizing the differences from previously reported γδ T cell-dependent mechanisms (McMenamin et al., 1994, supra; Zuany-Amorim et al., 1998, supra). To compare the results described herein with earlier studies, the more extensive systemic sensitization protocol of previous studies, involving seven intraperitoneal injections of OVA over 14 days, was evaluated. Using these conditions, differences in AHR between wild-type and γδ T cell-deficient mice were no longer observed, in agreement with the earlier studies (data not shown). The previous findings of γδ T cell-dependent lung eosinophilic infiltrates was also confirmed (data not shown). Thus, extensive systemic sensitization seems to promote immune-dependent facets of γδ T-cell functions, including γδ T cell-dependent eosinophilia. Whether or not γδ T cells arem actually capable of recognizing OVA remains undetermined. The present findings in the TCR-β$^{-/-}$ mice sensitized and challenged with OVA do not specifically address allergen-specific activation of γδ T cells in the development of AHR or eosinophilic inflammation. In TCR-γδ$^{-/-}$ mice depleted with monoclonal antibody against TCR-β and exposed to airway aerosolized OVA alone, airway responsiveness was slightly diminished (FIGS. 3C and 3D). Therefore, it remains possible that three exposures to aerosolized OVA alone activate αβ T cells, especially when the negative regulation by γδ T cells is absent.

Because the regulatory effects on AHR in the conditions of the present study were associated with a reduction in eosinophil infiltration, eosinophil-independent mechanisms must be considered, although eosinophil activation itself was not monitored. The cell entities that γδ T cells could influence include alveolar macrophages, airway epithelial cells and airway smooth muscle cells. γδ T cells have already been implicated in regulatory effects involving alveolar macrophages in tuberculosis. γδ T cells can alter the development of alveolar macrophage populations, as untreated TCR-δ$^{-/-}$ mice have lower macrophage cell counts in BAL fluid than their T cell-sufficient control counterparts (data not shown). This action could relate to the finding that TCR-δ$^{-/-}$ mice are deficient in monocyte chemoattractant protein 1 (DiTirro et al., 1998, *Infec. Immun.* 66:2284-2289). Airway epithelial cells are another source of reactive mediators leading to AHR (King et al., 1999, *J. Imunol.* 162:5033-5036). The intraepithelial/submucosa localization of γδ T cells facilitates their reaction to epithelial cell changes. As do other intraepithelial γδ T cells, lung γδ T cells may provide mediators for epithelial repair processes and other epithelial responses elicited by AHR-inducing stimuli. Furthermore, intraepithelial/submucosa ybT cells could exert their regulatory effects directly on airway smooth muscle cells, for example, by modifying secretin of smooth muscle cell derived cytokines, such as GM-CSF, IL-5 and IL-4.

In summary, these data demonstrate a previously unknown, αβ T cell-independent and probably also B cell-independent mechanism of airway regulation by γδ T cells. This mechanism may co-exist with immunoregulatory effects of γδ T cells on αβ T cell-dependent pathways of AHR.

Example 6

The following example demonstrates that airway hyperresponsiveness is increased in the absence of tumor necrosis factor-α (TNF-α), and that γδ T cells play a role in the failure of TNF-α transgenic mice to develop airway hyperresponsiveness.

Airway Hyperresponsiveness is Increased in the Absence of TNF-α

First, airway responsiveness to inhaled Mch was assessed in TNF-α deficient mice. Female C57BL/6 mice from 8 to 10 weeks of age were purchased from the Jackson Laboratories (Bar Harbor, Me.). Mice genetically deficient for TNF-α were a gift from Dr. John Harty, University of Iowa, Iowa City, Iowa. These mice were originally derived from intercrosses of (129Sv×C57BL/6)F1 mice heterozygous for the mutated 129/Sv TNF-αgene and maintained as a line of mixed 129/B6 genetic background homozygous for the mutation since 1996. The mice were maintained on OVA-free diets. All experimental animals used in this study were under a protocol approved by the Institutional Animal Care and Use Committee of the National Jewish Medical and Research Center.

Both OVA-sensitized and non-sensitized TNF-α deficient mice were challenged with an aerosol of OVA on three consecutive days, in parallel with C57BL/6 controls. Briefly, each strain of mouse was grouped based on the following treatments (4 mice/group/experiment): (a) airway challenge (×3) with OVA nebulization alone (N group); or (b) intraperitoneal sensitization with OVA and OVA airway challenge (IPN group). Mice were sensitized by intraperitoneal injection of 20 μg of OVA (Grade V; Sigma) emulsified in 2.25 mg alum (AlumImuject; Pierce, Rockford, Ill.) in a total volume of 100 μl on days 0 and 14. Mice were challenged via the airways to OVA (1% in saline) for 20 min. on days 28, 29 and 30 by ultrasonic nebulization (De Vilbiss, particle size 1-5 μm). Lung resistance ($R_L$) and dynamic compliance (Cdyn) were assessed 48 hrs after the last allergen challenge, and the mice were sacrificed to obtain tissues and cells for further assays. Airway resistance and Cdyn were determined as described above in Example 1.

Following OVA sensitization and challenge, C57BL/6 mice developed significant increases in RL and decreases in Cdyn in a dose-dependent manner, compared to mice only challenged with OVA (data not shown). Mice genetically deficient in TNF-α developed AHR and to a greater extent than the C57BL/6 animals. In non-sensitized mice receiving airway challenge alone, the degree of responsiveness was only slightly higher in the TNF-α deficient mice.

The number and types of inflammatory cells in the airways of TNF-α sufficient and deficient mice were measured in bronchoalveolar lavage fluid (BALF) (data not shown). Briefly, after assessment of $R_L$ and Cdyn, lungs were lavaged via the tracheal tube with Hank's balanced salt solution, (HBSS, 1×1 ml, 37° C.). The volume of collected BALF was measured in each sample and the number of BALF cells was counted by cell counter (Coulter Counter; Coulter Co., Hialeah, Fla.). Cytospin slides were stained with Leukostat (Fisher Diagnostics, Pittsburgh, Pa.) and differentiated in a blinded fashion by counting at least 300 cells under light microscopy.

Cytokine levels (IL-4, IL-5, IL-10, and IFN-γ) in BALF supernatants were measured by ELISA as described in Example 4 above. Cytokine levels were determined by comparison with the known standards. The limits of detection were 4 pg/ml. In C57BL/6 mice, sensitization and challenge to OVA resulted in a marked increase in inflammatory cell numbers compared with challenge alone. TNF-α deficient mice showed a similar inflammatory cell response, but the numbers of eosinophils in BALF were significantly lower than in C57BL/6 mice (data not shown).

Inflammatory cells were also measured in the peribronchial and perivascular tissue.

Briefly, lung cells were isolated as previously described (28) and passed through nylon wool columns to yield an enriched T cell preparation containing >90% CD3+cells. For cytofluorographic analysis, mAbs were conjugated with N-hydroxysuccinimido-biotin (Sigma) and/or fluorescein isothiocyanate isomer I on Celite (Sigma). Then, $1-2 \times 10^6$ cells in 96-well plates (Falcon-Becton Dickinson, Franklin Lakes, N.J.) were stained by using one- or two-color techniques and analyzed cytofluorographically on XL2 (Coulter, Miami, Fla.) counting 150,000 events per gated region. For each of the gated populations, mean fluorescence intensity (MFI) was examined to assess shifts in fluorescence of the examined populations. Streptavidin-phycoerythrin (diluted at 1:100 per $1 \times 10^6$ cells, Tago Immunologicals Biosource, Camarillo, Calif.) was used for the biotin-conjugated antibodies to enhance detection.

In mice challenged only, very little inflammatory cell infiltration was detected whereas intraperitoneal sensitization and subsequent challenge with OVA via the airways increased the number of eosinophils and lymphocytes at these sites. Inflammatory cell infiltration in sensitized/challenged TNF-α deficient mice was similar to that in sensitized and challenged C57BL/6 animals (data not shown).

γδ T Cells in SP-C-TNF-α Transgenic Mice.

For the following experiments, mice expressing the TNF-α gene under the control of the surfactant SP-C promotor (SP-C-TNF-α transgenic mice) were a gift from Dr. Yoshitaka Miyazaki, Department of Clinical Immunology, Medical Institute of Bioregulation, Kyushu University, Beppu, Japan. The transgenic founder mice (C57BL/6×DBA/2 F1) were backcrossed with C57BL/6 mice to generate F1 hybrid transgenic mice and maintained as a heterozygous line by repeated backcrossing since 1995. All transgenic mice were identified by PCR analysis of genomic DNA. Littermate transgene-negative mice were used as controls.

An increased frequency of γδ T cells has been demonstrated in the SP-C-TNF-α transgenic mice (Nakama et al., *Exp. Lung Res.*, 24:57-70, 1998). The present inventors therefore investigated the effects of TCR-δ mAb on the γδ T cell populations in the lung in OVA sensitized and challenged TNF-α deficient and transgenic mice. Briefly, depletion was achieved following injection of 200 μg hamster IgG mAb anti-TCR-δ (1:1 mixture of GL3 and 403A10) into the tail vein 3 days prior to the first OVA challenge. Sham-depletion was carried out using hamster IgG (Jackson Laboratories, Bar Harbor, Me.). OVA sensitization and challenge was carried out as described above. γδ T cells in the lung were analyzed by flow cytometric analysis.

The number of γδ T cells in the lung in TNF-α deficient mice was significantly lower than in normal C57BL/6 mice (data not shown). In contrast, the number of γδ T cells in the transgenic mice was significantly increased compared to littermate transgene-negative mice. Injection of TCR-δ mAb significantly suppressed the numbers of γδ T cells in the lung in sensitized and challenged transgenic mice as well as in C57BL/6 and littermate transgene-negative mice; the lower numbers in the TNF-α deficient mice did not change significantly (data not shown).

Airway Responsiveness in TNF-α Transgenic Mice Following γδ T cell Depletion.

As described in Examples 1-6, the present inventors demonstrated that γδ cells play a role in the regulation of airway responsiveness (Examples 1-6 and Lahn et al., *Nature Med.*, 5:150-1156, 1999). In view of the increased number of γδ T cells in the TNF-α transgenic mice (Nakama et al., *Exp. Lung Res.*, 24:57-70, 1998) and the findings that γδ T cells are activated by TNF-α (more so than αβ T cells) (Lahn et al., *J. Immunol.*, 160:5221-5230, 1998), the present inventors examined whether activated γδ T cells might play a role in the failure of TNF-α transgenic mice to develop AHR. To deplete γδ T cells, TNF-α transgenic mice and TNF-α deficient mice were treated with TCR-δ mAb 3 days before the first challenge. TNF-α deficient mice administered anti-TCR-δ failed to show any further increase in AHR (data not shown). In contrast, SP-C-TNF-α transgenic mice depleted of γδ T cells developed AHR while sham-treated controls did not (data not shown). This effect on AHR was not correlated with a cellular inflammatory response: in both OVA sensitized and challenged TNF-α deficient and transgenic mice, there were no significant differences in the composition of inflammatory cells in the BALF following depletion of γδ T cells (data not shown).

In summary, these data confirm that γδ T cells play an important role in the pathophysiology of the development of AHR and, based on the data in the SP-C-TNF-α transgenic mice, a possibility as to the mechanism is suggested. Thus, the interactions between TNF-α and γδ T cells may be central in regulating airway tone following airway exposure to allergen. These findings emphasize complex but important contributions of TNF-α to the overall regulation of allergic inflammatory responses in the lung and the development of altered airway function in part through interactions with γδ T cells. The additional finding that the absence of TNF-α was associated with increased levels of IL-10, an important factor in the development of AHR, reveals another potential mechanism by which TNF-α may control airway responsiveness, that is through suppression of IL-10.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to reduce airway hyperresponsiveness in a mammal, comprising administering to a mammal a phosphoantigen that activates γδ T cells, wherein the activation of said γδ T cells reduces airway hyperresponsiveness in said mammal and said mammal has, or is at risk of developing, a respiratory condition associated with airway hyperresponsiveness.

2. The method of claim 1, wherein the phosphoantigen comprises isoprenylpyrophosphate (IPP).

3. The method of claim 1, wherein said phosphoantigen is administered so that the number of γδ T cells in the lung tissue of said mammal increases.

4. The method of claim 1, wherein said phosphoantigen is administered so that γδ T cells in said mammal are activated.

5. The method of claim 1, wherein said phosphoantigen is targeted to γδ T cells in the lung tissue of said mammal.

6. The method of claim 1, wherein said phosphoantigen is targeted to γδ T cells having a T cell receptor (TCR) selected from the group consisting of a murine TCR comprising Vγ4 and a human TCR comprising Vγ1.

7. The method of claim 1, wherein said phosphoantigen is administered by a route selected from the group consisting of inhaled, intratracheal and nasal routes.

8. The method of claim 1, wherein said phosphoantigen is administered to said mammal in an amount effective to reduce airway hyperresponsiveness in said mammal as compared to prior to administration of said phosphoantigen.

9. The method of claim 1, wherein said phosphoantigen is administered with a pharmaceutically acceptable excipient.

10. The method of claim 1, wherein said phosphoantigen is administered within between about 1 hour and 6 days of an initial diagnosis of airway hyperresponsiveness in said mammal.

11. The method of claim 1, wherein said phosphoantigen is administered within less than about 72 hours of an initial diagnosis of airway hyperresponsiveness in said mammal.

12. The method of claim 1, wherein said phosphoantigen is administered prior to development of airway hyperresponsiveness in said mammal.

13. The method of claim 1, wherein increasing γδ T cell action by administration of said phosphoantigen decreases airway methacholine responsiveness in said mammal.

14. The method of claim 1, wherein increasing γδ T cell action by administration of said phosphoantigen reduces airway hyperresponsiveness of said mammal such that the $FEV_1$ value of said mammal is improved by at least about 5%.

15. The method of claim 1, wherein increasing γδ T cell action by administration of said phosphoantigen improves said mammal's $PC_{20methacholine}FEV_1$ value such that the $PC_{20methacholine}FEV_1$ value obtained before increasing γδ T cell action when the mammal is provoked with a first concentration of methacholine is substantially the same as the $PC_{20methacholine}FEV_1$ value obtained after increasing γδ T cell action when the mammal is provoked with double the amount of the first concentration of methacholine.

16. The method of claim 15, wherein said first concentration of methacholine is between about 0.01 mg/ml and about 8 mg/ml.

17. The method of claim 1, wherein said airway hyperresponsiveness is associated with a disease selected from the group consisting of chronic obstructive disease of the airways and asthma.

18. A method to reduce airway hyperresponsiveness in a mammal, comprising administering to a mammal a composition consisting essentially of a phosphoantigen that activates γδ T cells, wherein the activation of said γδ T cells reduces airway hyperresponsiveness in said mammal and said mammal has, or is at risk of developing, a respiratory condition associated with airway hyperresponsiveness.

19. The method of claim 1, wherein the mammal is a human.

* * * * *

UNITED STATES PATENT AND TRADEMARK OFFICE
CERTIFICATE OF CORRECTION

PATENT NO. : 7,582,300 B2  Page 1 of 1
APPLICATION NO. : 10/808846
DATED : September 1, 2009
INVENTOR(S) : Gelfand et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 815 days.

Signed and Sealed this

Fourteenth Day of September, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:synthetic
      peptide

```
-continued

<220> FEATURE:
<221> NAME/KEY: VARIANT
<222> LOCATION: (1)..(7)

<400> SEQUENCE: 1

Phe Ala Leu Gln Leu Glu Leu
 1               5

<210> SEQ ID NO 2
<211> LENGTH: 7
<212> TYPE: PRT
<213> ORGANISM: Mycobacterium leprae

<400> SEQUENCE: 2

Phe Gly Leu Gln Leu Glu Leu
 1               5
```